United States Patent [19]
Jung et al.

[11] Patent Number: 5,972,998
[45] Date of Patent: Oct. 26, 1999

[54] TRIPTOLIDE DERIVATIVES USEFUL IN THE TREATMENT OF AUTOIMMUNE DISEASES

[75] Inventors: Michel J. Jung, Lawrence, Kans.; Mahinda Wickramaratne, Rukgahawila, Sri Lanka; Michael Hepperle, St. Louis, Mo.

[73] Assignee: Hoechst Marion Roussel, Inc., Bridgewater, N.J.

[21] Appl. No.: 09/076,591

[22] Filed: May 12, 1998

Related U.S. Application Data

[60] Provisional application No. 60/108,155, May 23, 1997.

[51] Int. Cl.$^6$ .......................... A61K 31/34; C07D 407/00
[52] U.S. Cl. .......................... 514/468; 549/297; 549/298
[58] Field of Search .......................... 514/468; 549/297, 549/298

[56] References Cited

U.S. PATENT DOCUMENTS

| | | | |
|---|---|---|---|
| 5,580,562 | 12/1996 | Lipsky et al. | 549/297 |
| 5,663,335 | 9/1997 | Qi et al. | 549/297 |

FOREIGN PATENT DOCUMENTS

| | | |
|---|---|---|
| 9113627 | 9/1991 | WIPO . |
| 9426265 | 11/1994 | WIPO . |

OTHER PUBLICATIONS

Chemical Abstracts, vol. 118, No. 19, May 10, 1993, Abstract No. 18277m, D.Q. Yu et al, "Structure modification of triptolide", p. 21, XP002073427, compound with CN(RN):141069–12–7, see abstract & Yaoxue Xuebao, vol. 27, No. 11, 1992, pp. 830–836.

Chemical Abstracts, vol. 119, No. 9, Aug. 30, 1993, Abstract No. 91202g, C.P. Zhang et al, "Diterpenoids from leaves of Tripterygium wildfordij", p. 649, XP002073428, compound with CN(RN):147809–20–9, see abstract & Yaoxue Xuebao, vol. 28, No. 2, 1993, pp. 110–115.

J. Am. Chem. Soc—94:20, pp. 7194–7195, (1972).

J. Am. Chem. Soc. 104, pp. 867–869, (1982).

Kutney, et al., Recl. Trav. Chim. Pays–Bas 115, pp. 77–93 (1996).

Gu Ke–xian, et al., Chinese Pharmacological Bulletin 10(1), pp. 54–57 (1994).

Zhang et al., Acta Pharmaceutica Sinica, vol. 28, No. 2, pp. 110–115 (1993).

Fu–xiao, et al., Acta Botanica Sinica, vol. 34, No. 8, pp. 618–621 (1992).

van Tamelen, et al., J. Am. Chem. Soc. vol. 104, No. 6, pp. 1785–1786 (1982).

*Primary Examiner*—Amelia Owens
*Attorney, Agent, or Firm*—Balaram Gupta

[57] ABSTRACT

The present invention relates to novel triptolide derivatives and a method of treating a patient suffering from an autoimmune disease comprising administering to a patient an effective amount of the novel triptolide derivatives.

36 Claims, No Drawings

TRIPTOLIDE DERIVATIVES USEFUL IN THE TREATMENT OF AUTOIMMUNE DISEASES

This application claims the priority of U.S. Provisional Application Ser. No. 60/108,155, filed May 23, 1997.

BACKGROUND OF THE INVENTION

Autoimmune and inflammatory diseases affect more than fifty million Americans. As a result of basic research in molecular and cellular immunology over the last ten to fifteen years, approaches to diagnosing, treating and preventing these immunological based diseases have been changed forever. By dissecting the individual components of the immune system, those cells, receptors and mediators which are critical to the initiation and progression of immune responses have been, and continue to be, elucidated. Crystallographic analysis of proteins encoded in the major histocompatability complex, identification of an antigen-specific T cell receptor, and development of a basic understanding of the complex cytokine network have all contributed to a revolution in immunology. Various immunosuppressive agents have proved to be useful in the prevention of transplantation rejection and in the treatment of autoimmune diseases such as rheumatoid arthritis, nephritis, uveitis, thyroiditis, and early stage of insulin dependent diabetes mellitus, systemic lupus erythematosus, psoriasis and inflammatory bowel disease.

The immune system when operating normally is involved in precise functions such as recognition and memory of, specific response to, and clearance of, foreign substances (chemical and cellular antigens) that either penetrate the protective body barriers of skin and mucosal surfaces (transplanted tissue and microorganisms such as bacteria, viruses, parasites) or arise de novo (malignant transformation). The arsenal of the immune response is composed of two major types of lymphocytes that are either B-lymphocytes (B cells, responsible for producing antibodies which attack the invading microorganisms) or the T-lymphocytes (T cells, responsible for eliminating the infected or abnormal target cells) in cooperation with macrophages. The cascade of principal events in the immune system is more fully described by I. Roitt, J. Brostoff and D. Male in "Immunology", 3rd edition, Mosby, 1993 which is herein incorporated by reference, and may be summarized as follows.

The response is initiated by the interaction of an antigen with macrophages and surface antibodies on B cells. The macrophages ingest and process the antigen. The activated macrophages secrete interleukin-1 (IL-1) and tumor necrosis factor (TNF), and display the processed antigen on the cell surface together with a major antihistocompatibility antigen. Both IL-1 and TNF initiate a number of processes involving inflammation. Also, IL-1 induces proliferation of B cells and synthesis of antibodies. But more importantly, IL-1 activates T cells which release a series of lymphokines including interleukin-2 (IL-2) that activate the proliferation of T cells and cytotoxic lymphocytes. In autoimmune diseases, the system is unable to distinguish between "non-self" antigen and "self" antigen and will start to produce autoantibodies or autoreactive T cells which attack the normal components of the body.

Each element in the cascade of the immune response may be considered as a potential site for pharmacological intervention. For example, adrenocorticosteroids act in the first stages of the immune response, interact with the macrophages and, inhibit the synthesis and release of IL-1. Other immunosuppressive agents used in the treatment of autoimmune diseases have been identified, such as azathioprine and methotrexate for rheumatoid arthritis, cyclophosphamide for nephritic conditions of immune origin, and cyclosporin for rheumatoid arthritis, uveitis, early onset insulin dependent diabetes mellitus, psoriasis, nephritic syndrome and aplastic anemia.

In addition, immunosuppressive agents have proved to be useful in preventing and treating organ transplantation rejection that may occur in allograft transplantation. In allograft transplantation one person donates an organ to a genetically disparate individual while in xenograft transplantation an organ of one species is transplanted into a member of another species. In those cases, the use of cyclosporin has shown a real improvement in the condition of the person receiving the organ. However, the therapeutic index of the available immunosuppressive drugs is narrow, none of the drugs are completely effective and their use has been limited by severe toxicity.

It has been established that various extracts and components of the extracts of *Tripterygium wilfordii* Hook F, an herbal plant from the Celastraceae family that is grown mainly in the southern part of China, are useful as immunosuppressive agents. Zhang, et al., *Shanghai Yike Da ue Xuebao*, 13(4), 267 (1986), have characterized *T. wilfordii* as comprising at least six different diterpenoids, including triptonide, triptolide, triptophenolide and triptonolide. More specifically, P. E. Lipsky, et al. in WO 91/13627, published Sep. 19, 1991, disclosed that extracts or components of the extracts of *Tripterygium wilfordii* Hook F are useful in suppressing autoimmune diseases, such as rheumatoid arthritis, systemic lupus erythematosus and psoriasis. Triptolide has been reported by Yang, et al, *Int. J. Immunopharmac.*, 14, 963 (1992) and Yang, et al., *Int. J. Immunopharmac.*, 16, 895 (1994), to suppress lymphocyte proliferation and skin allograft rejection. In addition, Jin and Wiedmann, in WO 94/26265, published Nov. 24, 1994, disclosed a composition wherein an additional component of *Tripterygium wilfordii* Hook F, purified 16-hydroxytriptolide, is administered in conjunction with another immunosuppressive agent, such as cyclosporin A, FK506, azathioprine, methotrexate, rapamycin, mycophenolic acid, or a glucocorticoid. The above composition was disclosed as providing an increase in immunosuppressive activity relative to the sum of the effects produced by 16-hydroxytriptolide or the other immunosuppressive agent used alone. This allowed for greater immunosuppressive activity with reduced toxicity in immunosuppressive therapy, such as in therapy for transplantation rejection and autoimmune disease. P. E. Lipsky, et al. disclosed in U.S. Pat. No. 5,580,562, published Dec. 3, 1996, a *Tripterygium wilfordii* Hook F preparation which has an improved LD50 in mice, an improved therapeutic activity:toxic index ratio and a lower amount of triptolide as compared to previous preparations.

SUMMARY OF THE INVENTION

The present invention provides novel compounds of the formula (I):

formula (I)

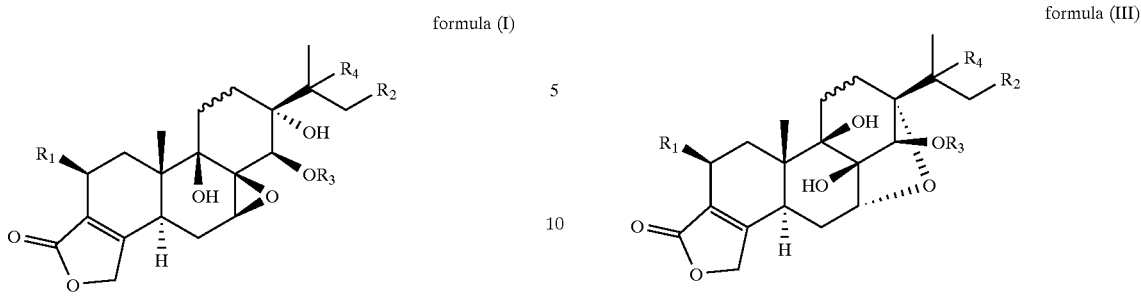

formula (III)

wherein ∼∼∼represents a single or double bond;

$R_1$ and $R_2$ are each independently is H or —$OR_5$;

$R_3$ is H, —C(=O)($CH_2$)$_n$$CO_2$H or a suitable amino acid;

$R_4$ is H or —OH;

$R_5$ is H, —C(=O)($CH_2$)$_n$$CO_2$H or a suitable amino acid;

n is the integer 2, 3, 4, 5 or 6; and the stereoisomers, enantiomers and pharmaceutically acceptable salts thereof;

provided that $R_1$ and $R_2$ are H when $R_3$ is other than H.

The present invention further provides novel compounds of the formula (II):

formula (II)

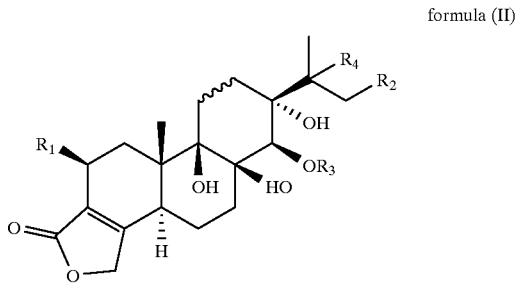

wherein ∼∼∼represents a single or double bond;

$R_1$ and $R_2$ are each independently is H or —$OR_5$;

$R_3$ is H, —C(=O)($CH_2$)$_n$$CO_2$H or a suitable amino acid;

$R_4$ is H or —OH;

$R_5$ is H, —C(=O)($CH_2$)$_n$$CO_2$H or a suitable amino acid;

n is the integer 2, 3, 4, 5 or 6; and the stereoisomers, enantiomers and pharmaceutically acceptable salts thereof;

provided that $R_1$ and $R_2$ are H when $R_3$ is other than H.

In addition, the present invention provides novel compounds of the formula (III):

wherein ∼∼∼represents a single or double bond;

$R_1$ and $R_2$ are each independently is H or —$OR_5$;

$R_3$ is H, —C(=O)($CH_2$)$_n$$CO_2$H or a suitable amino acid;

$R_4$ is H or —OH;

$R_5$ is H, —C(=O)($CH_2$)$_n$$CO_2$H or a suitable amino acid;

n is the integer 2, 3, 4, 5 or 6; and the stereoisomers, enantiomers and pharmaceutically acceptable salts thereof;

provided that $R_1$ and $R_2$ are H when $R_3$ is other than H.

The present invention further provides novel intermediates for the preparation of compounds of formulas (I), (II) and (III). In addition, the present invention provides a method of treating a patient suffering from an autoimmune disease comprising administering to a patient an effective amount of a compound of formulas (I), (II) or (III).

DETAILED DESCRIPTION OF THE INVENTION

The term "stereoisomers" is a general term for all isomers of individual molecules that differ only in the orientation of their atoms in space. It includes geometric (cis/trans) isomers, and isomers of compounds with more than one chiral center that are not mirror images of one another (diastereomers). The term "chiral center" refers to a carbon atom to which four different groups are attached. The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction. The term "racemic mixture" or "racemic modification" refers to a mixture of equal parts of enantiomers and which are optically inactive. As used herein the prefixes "(+)" and "(−)" are employed to designate the sign of rotation of plane polarized light by the compound, with (+) meaning the compound is dextrorotatory and (−) meaning the compound is levorotatory. For amino-acids, the designations L/D, or R/S can be used as described in IUPAC-IUB Joint Commission on Biochemical Nomenclature, Eur. J. Biochem. 138: 9–37 (1984).

The term "Pharmaceutically acceptable salt" is a nontoxic organic or inorganic acid addition salt of the base compounds represented by formulas (I), (II) or (III), or any of their intermediates. Some examples of inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Examples of such acids are acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methane sulfonic acid and 2-hyroxyethane sulfonic acid. Such salts can exist in either a hydrated or substantially anhydrous form.

The term "enantiomeric enrichment" refers to the increase in the amount of one enantiomer as compared to its corresponding opposite enantiomer. A convenient method of expressing enantiomeric enrichment achieved is the concept of "enantiomeric excess" or "ee", which is expressed by the following equation;

$$ee = \frac{E^1 - E^2}{E^1 + E^2} \times 100$$

in which $E^1$ is the amount of the first enantiomer and $E^2$ is the amount of the second corresponding enantiomer. For example, where the initial ratio of two enantiomers in a reaction is 50:50 (a racemic mixture) and the reaction produces enantiomeric enrichment with a final ratio of 90:10, then the ee with respect to the first enantiomer is 80%.

The designation "◄" refers to a bond that protrudes forward out of the plane of the page.

The designation "⋯⋯" refers to a bond that protrudes backward out of the plane of the page.

The designation "〰〰" as used herein refers to a single or double bond.

A numbering system for triptolide as disclosed in the literature is shown below.

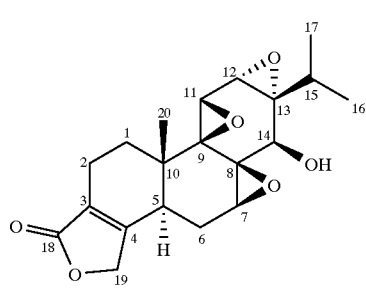

It is understood by one of ordinary skill in the art that modifications of triptolide can result in changes in the above numbering system. Triptolide in its optically active form and racemic form is readily available to one of ordinary skill in the art. Triptolide, in optically active form, can be isolated from the natural source *Tripterygium wilfordii* following the procedure of S. M. Kupchan, et al., *J. Am. Chem. Soc*, 94, 7194 (1972). Alternatively, triptolide can be prepared in its racemic form following the total synthesis of Chee Kong Lai, et al., *J. Org. Chem.*, 47, 2364–2369 (1982), van Tamelen and Leiden, *J Am. Chem. Soc.*, 104, 1785 (1982) or Garver and van Tamelen, *J. Am. Chem. Soc.*, 104, 867 (1982). Additional starting materials can be obtained as described by Kutney and Han, *Recueil des Travaux Chimiques des Pays-Bas*, 115(01) 77 (1996), Deng Fu-xiao, et al., *Acta Botanica Sinica*, 34(8), 618 (1992), C. P. Zhang, *Acta Pharmaceutica Sinica*, 28(2), 110 (1993) and Jin and Wiedmann, WO 94/26265, published Nov. 24, 1994.

As used herein "Tripdiolide" or "2-Hydroxytriptolide" are the same and have the following structure;

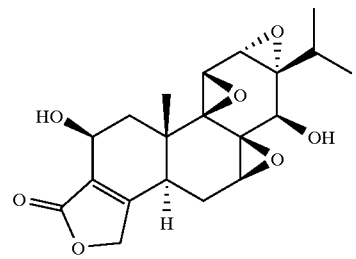

As used herein "Triptolidenol" and "15-Hydroxytriptolide" are the same have the following structure;

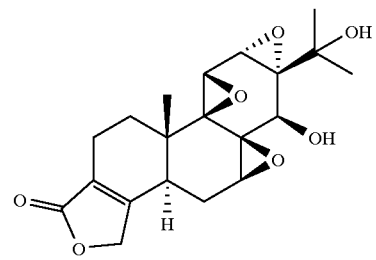

As used herein "Tripterinin" and "16-Hydroxytriptolide" are the same and have the following structure;

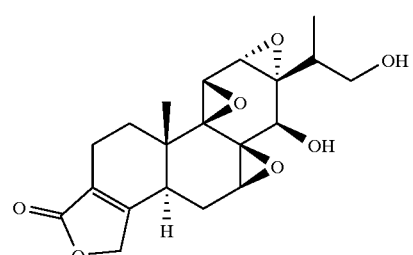

As used herein each a-amino acid has a characteristic "R-group", the R-group being the side chain, or residue, attached to the a-carbon atom of the a-amino acid. For example, the R-group side chain for glycine is hydrogen, for alanine it is methyl, for valine it is isopropyl. For the specific R-groups or side chains of the a-amino acids see A. L. Lehninger's text on Biochemistry.

Unless otherwise stated, the a-amino acids utilized in the compounds of the present invention are preferably in their L-configuration; however, applicants contemplate that the amino acids employed herein can be of either the D- or L-configurations or can be mixtures of the D- and L-isomers, including the racemic mixture. The recognized abbreviations for the a-amino acids are set forth in Table I.

TABLE I

| AMINO ACID | SYMBOL |
| --- | --- |
| alanine | Ala or A |
| arginine | Arg or R |
| asparagine | Asn or N |
| aspartic acid | Asp or D |
| cysteine | Cys or C |
| glutamine | Gln or Q |
| glutamic acid | Glu or E |
| glycine | Gly or G |
| histidine | His or H |
| isoleucine | Ile or I |
| leucine | Leu or L |
| lysine | Lys or K |
| methionine | Met or M |
| phenylalanine | Phe or F |
| proline | Pro or P |
| serine | Ser or S |
| threonine | Thr or T |
| tryptophan | Trp or W |
| tyrosine | Tyr or Y |
| valine | Val or V |

As used herein the term "suitable amino acid" refers to the amino acids listed in table I above. The suitable amino acid is connected to the compound of formulas (I), (II) or (III) at the carboxy end of the amino acid, resulting in an ester linkage. For example, addition of glutamic acid at the —OH at position 14 of formula (I) provides a compound with the following structure:

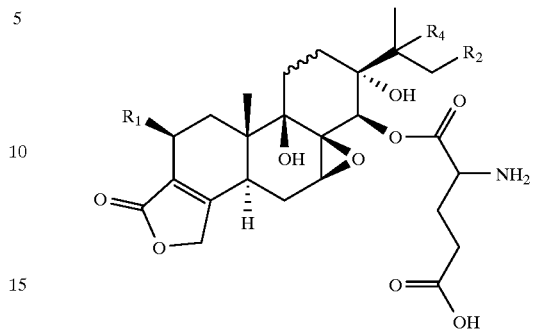

Preferred suitable amino acids are Ala, Phe, Glu, Lys and Arg, with Ala, Glu and Lys being most preferred.

The compounds of formulas (Ia) and (IIa) can be prepared as described in Scheme A. All substituents, unless otherwise indicated, are previously defined. The reagents and starting materials are readily available to one of ordinary skill in the art.

Scheme A

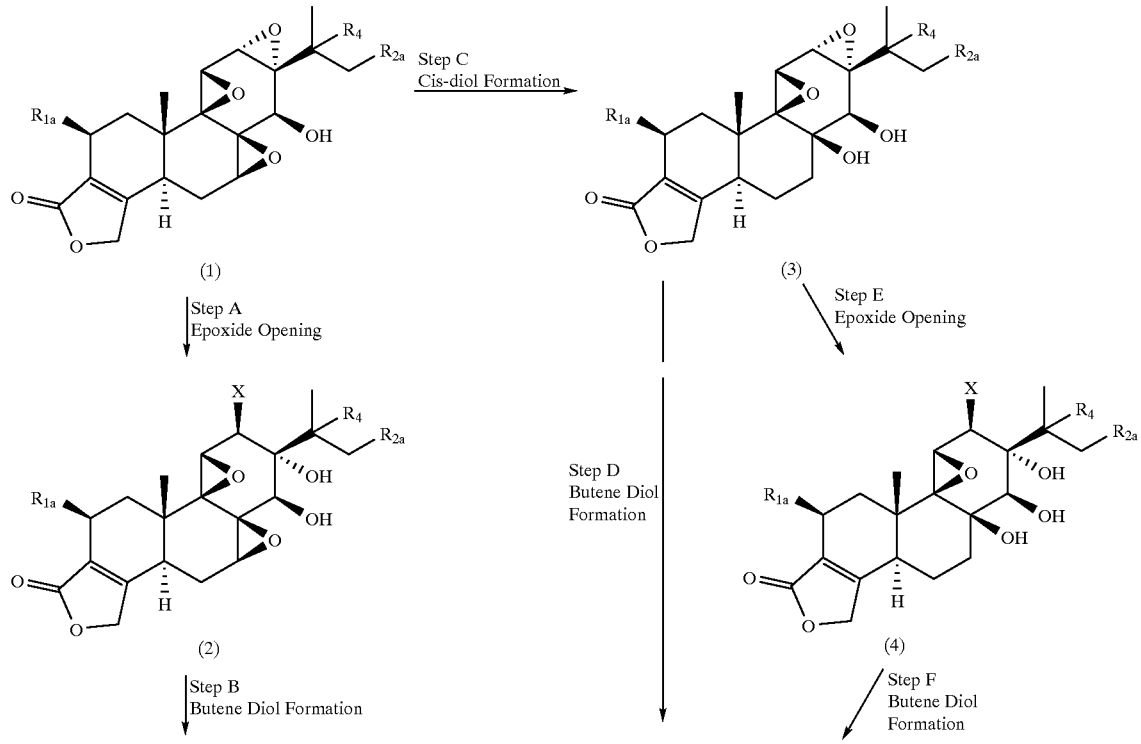

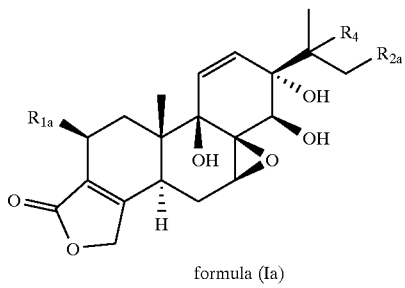

formula (Ia)

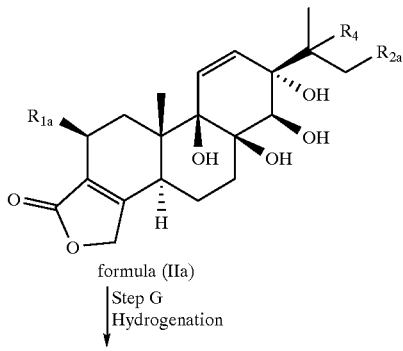

formula (IIa)

Step G
Hydrogenation

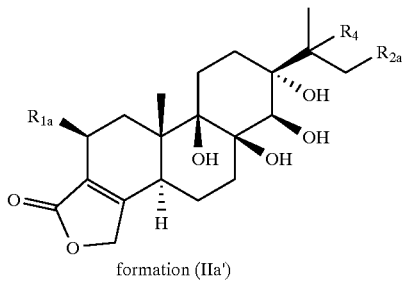

formation (IIa')

In Scheme A, step A the 12-13 epoxide on the compound of structure (1) wherein $R_{1a}$ and $R_{2a}$ are each independently hydrogen or —OH and X is Cl or Br, is opened to provide the compound of structure (2). More specifically, compound (1) is dissolved in a suitable organic solvent, such as acetone or dioxane, and treated with a suitable aqueous acid, such as 2N HCl or 30% HBr. The reaction is stirred for about 1 to 5 hours at a temperature of about 23° C. to about 70° C. The reaction is then diluted with water and the compound of structure (2) is isolated and purified by techniques well known in the art, such as extraction techniques, chromatography and/or recrystallization. For example, the reaction mixture is extracted with a suitable organic solvent, such as methylene chloride or ethyl acetate. The organic extracts are combined, rinsed with brine, dried over anhydrous magnesium sulfate, filtered and concentrated under vacuum to provide the crude product (2). The crude product is then purified by recrystallization from a suitable solvent system, such as hexane/methylene chloride to provide the purified compound of structure (2).

In Scheme A, step B the compound of structure (2) is converted to the butene diol of formula (Ia). For example, compound (2) is combined with Pd/BaSO$_4$ and sodium acetate in a suitable organic solvent, such as ethanol. The reaction mixture is then placed under an atmosphere of hydrogen at room temperature for about 3 hours with stirring. The product is then isolated and purified by techniques well known in the art. For example, the reaction is filtered through diatomaceous earth and the filtrate is concentrated under vacuum. The residue is then purified by preparative thin layer chromatography (prep TLC) on silica gel with a suitable eluent, such as methanol/chloroform to provide the purified compound of formula (Ia).

In Scheme A, step C the compound of structure (1) is subjected to cis-diol formation conditions to produce the compound of structure (3). For example, the compound of structure (1), such as triptolide is dissolved in a suitable anhydrous organic solvent, such as tetrahydrofuran under an inert atmosphere, such as nitrogen at room temperature. The solution is treated with about 4 to about 6 equivalents of sodium cyanoborohydride followed by dropwise addition of about 1.2 equivalents of neat boron trifluoride diethyl etherate (BF$_3$/Et$_2$O). The reaction mixture is allowed to stir for about 1 hour to about 24 hours, with about 16 hours being preferred. The reaction is then quenched by addition of aqueous ammonium chloride and the product is isolated and purified by techniques well known in the art, such as extraction techniques and chromatography.

For example, the quenched reaction mixture is extracted with a suitable organic solvent, such as methylene chloride. The organic extracts are combined, rinsed with brine, dried over anhydrous magnesium sulfate, filtered and concentrated under vacuum to provide the crude product. The crude product is then purified by flash chromatography on silica gel with a suitable eluent, such as methanol/chloroform to provide the purified compound of structure (3).

Alternatively, the compound of structure (3) can be prepared by dissolving the compound of structure (1) in a suitable anhydrous organic solvent, such as tetrahydrofuran under an inert atmosphere, such as nitrogen, at room temperature. To this is added about 1.9 equivalents of lithium borohydride followed by addition of about 2.1 equivalents of neat boron trifluoride diethyl etherate. The reaction mixture is allowed to stir for about 1 hours to about 2 hours, with about 1.5 hours being preferred. The reaction is then carefully quenched with 1N HCl and the product is isolated and purified by techniques well known in the art, such as extraction techniques and chromatography.

For example, the quenched reaction is extracted with a suitable organic solvent, such as methylene chloride. The organic extracts are combined, rinsed with 1N sodium bicarbonate, brine, dried over anhydrous magnesium sulfate, filtered and concentrated under vacuum to provide the crude product. The crude product is then purified by flash chromatography on silica gel with a suitable eluent, such as 20% ethyl acetate/hexane to provide the purified compound of structure (3).

In Scheme A, step D the compound of structure (3) is converted to the butene diol of formula (IIa). For example, compound (3) is dissolved in a suitable organic solvent, such as chloroform under an atmosphere of nitrogen at room temperature. The solution is treated with 1.1 equivalents of iodo trimethylsilane and 0.5 equivalents of triphenylphoshine. The reaction mixture is stirred for about 10 minutes and then poured into water. The product is then isolated and purified by techniques well known in the art, such as extraction techniques and flash chromatography. For example, the quenched reaction mixture is extracted with a suitable organic solvent, such as ethyl acetate, the combined organic extracts are washed with 10% aqueous sodium thiosulfate, brine, dried over anhydrous magnesium sulfate, filtered and concentrated under vacuum to provide the crude product of formula (IIa). The crude material is purified by flash chromatography on silica gel with a suitable eluent, such as 40% ethyl acetate/hexane to provide the purified compound of formula (IIa).

Alternatively, the compound of formula (IIa) can be prepared from compound (3) via steps E and F. More specifically, in Scheme A, step E the 12-13 epoxide of compound (3) is opened to provide the compound of structure (4). For example, the compound (3) is combined with 1.5 equivalents of tetrabutyl ammonium bromide in a suitable organic solvent, such as methylene chloride at room temperature under an atmosphere of nitrogen. The reaction is then treated with 2.0 equivalents of neat boron trifluoride diethyl etherate and the reaction mixture is then allowed to stir for about 30 minutes. Water is then added to quench the reaction and the product is isolated and purified by techniques well known in the art, such as extraction techniques and flash chromatography. For example, the quenched reaction mixture is diluted with water and extracted with a suitable organic solvent, such as methylene chloride. The combined organic extracts are washed with water, brine, dried over anhydrous magnesium sulfate, filtered and concentrated under vacuum to provide the crude compound (4). The crude material is then purified by flash chromatography on silica gel with a suitable eluent, such as 40% ethyl acetate/hexane to provide the purified compound (4).

In Scheme A, step F, compound (4) is converted to the butene diol of formula (IIa). More specifically, compound (4) is dissolved in a suitable organic solvent, such as acetonitrile and treated with 5 equivalents of freshly activated zinc powder. Then 20 equivalents of concentrated HCl is added to the slurry and the reaction mixture is stirred for about 10 minutes. The reaction is then diluted with water and the acetonitrile is removed under vacuum. The remaining aqueous phase is extracted with a suitable organic solvent, such as ethyl acetate, the organic extracts are combined, washed with 1N sodium bicarbonate, brine, dried over anhydrous magnesium sulfate, filtered and concentrated under vacuum to provide the crude compound of formula (IIa). The crude material is then purified by flash chromatography on silica gel with a suitable eluent, such as 40% ethyl acetate/hexane to provide the purified compound of formula (IIa).

In Scheme A, step G the compound of formula (IIa) is hydrogenated to provide the compound of formula (IIa). For example, the compound of formula (IIa) is dissolved in a suitable organic solvent, such as benzene and a catalytic amount of Wilkinson's Catalyst [tris(triphenylphosphine) rhodium(I) chloride], is added. The reaction mixture is stirred under an atmosphere of hydrogen for about 24 hours at room temperature. The reaction is then filtered through a short neutral alumina column and the filtrate is concentrated under vacuum to provide the crude compound of formula (IIa'). The crude material is purified by techniques well known in the art, such a preparative TLC on silica gel with a suitable eluent, such as methanol/chloroform to provide the purified compound of formula (IIa').

The compounds of formula (IIIa) can be prepared as described in Scheme B. All substituents, unless otherwise indicated, are previously defined. The reagents and starting materials are readily available to one of ordinary skill in the art.

Scheme B

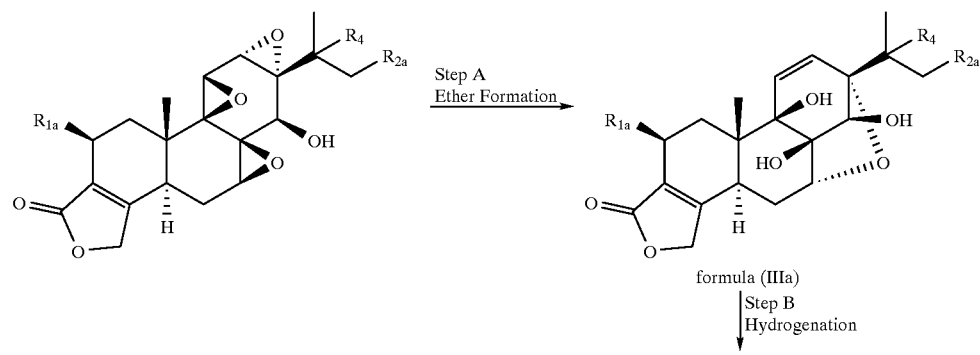

formula (IIIa)

Step B
Hydrogenation

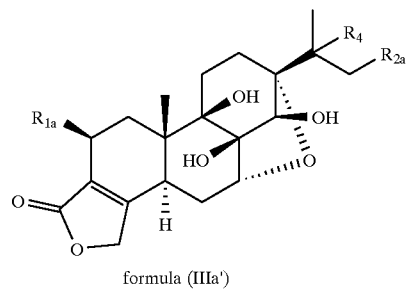

formula (IIIa')

In Scheme B, step A the compound of structure (1) is converted to the 7-13 ether of formula (IIIa). For example, the compound (1) is dissolved in a suitable organic solvent, such as acetonitrile under an inert atmosphere, such as nitrogen. The solution is then treated by dropwise addition with a solution of about 1.2 equivalents triphenylphosphine and about 6.3 equivalents iodine in a suitable organic solvent, such as acetonitrile, at room temperature. The reaction mixture is then stirred for about 10 minutes at room temperature and then at about 75° C. for about 2 hours. The acetonitrile is then removed under vacuum and the residue is treated with water. The aqueous suspension is then extracted with a suitable organic solvent, such as ethyl acetate, the organic extracts are combined, washed with 10% aqueous sodium bisulfite, brine, dried over anhydrous magnesium sulfate, filtered and concentrated under vacuum to provide the crude compound of formula (IIIa). The crude material is then purified by flash chromatography on silica gel with a suitable eluent, such as methanol/chloroform to provide the purified compound of formula (IIIa).

In Scheme B, step B the compound of formula (IIIa) is hydrogenated to the compound of formula (IIIa'). For example, the compound of formula (IIIa) is dissolved in a suitable organic solvent, such as ethanol and treated with a catalytic amount of Pd on $BrCO_3$. The reaction mixture is placed under an atmosphere of hydrogen and stirred for about 12 hours at room temperature. The reaction is then carefully filtered and the filtrate is concentrated under vacuum to provide the crude compound of formula (IIIa'). The crude material is purified by techniques well known in the art such as flash chromatography on silica gel with a suitable solvent, such as ethyl acetate/hexane to provide the purified title compound of formula (IIIa').

The compounds of formula (Ib) can be prepared as described in Scheme C. All substituents, unless otherwise indicated, are previously defined. The reagents and starting materials are readily available to one of ordinary skill in the art.

Scheme C

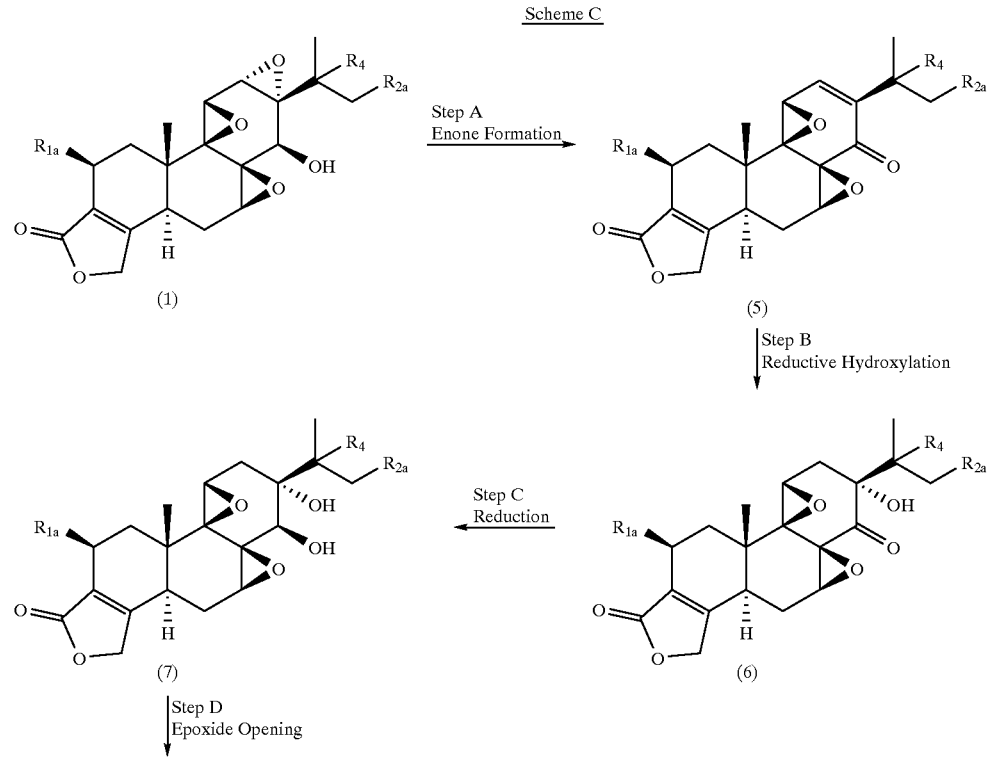

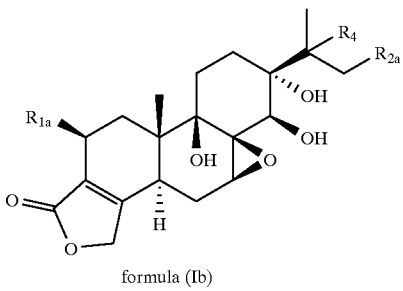

formula (Ib)

In Scheme C, step A the compound of structure (1) is converted to the enone of structure (5). For example, compound (1) is dissolved in a suitable organic solvent, such as methylene chloride under an inert atmosphere, such as nitrogen. The solution is then treated with 1.6 equivalents of triethylamine and 1.5 equivalents of triethylsilyl triflate. The reaction mixture is then stored at a temperature of about 4° C. for about 12 hours. The reaction is then warmed to room temperature and an additional 1.5 equivalents of triethylsilyl triflate is added. The reaction mixture is then stirred for 6 hours at room temperature, then poured into water and neutralized with saturated aqueous sodium bicarbonate solution. The phases are separated and the aqueous phase is extracted with a suitable organic solvent, such as methylene chloride. The organic phase and organic extract are combined, washed with 2 N aqueous HCl, brine, dried over anhydrous magnesium sulfate, filtered and concentrated under vacuum to provide crude enone (5). The crude material is then purified by flash chromatography on silica gel with a suitable eluent, such as chloroform or methanol/chloroform to provide the purified enone (5).

In Scheme C, step B the enone (5) is reductively hydroxylated to the ketone of structure (6). For example, the enone (5) is dissolved in a suitable anhydrous organic solvent, such as tetrahydrofuran under an inert atmosphere, such as nitrogen and the solution is cooled to about −78° C. The solution is then treated dropwise with 1.1 equivalents of LS-Selectride® (1.0 M solution of lithium trisiamylborohydride in THF, available from Aldrich Chemical Company, Inc., Milwaukee, Wis.). The reaction is allowed to stir for about one hour, quenched by addition of CELITE®/MgSO$_4$7H$_2$O and then allowed to warm to room temperature. The resulting slurry is then filtered through diatomaceous earth and the solids are washed with a suitable organic solvent, such as diethyl ether. The filtrate is then poured into water which is then acidified with 2N aqueous HCl. The phases are separated and the aqueous phase is extracted with a suitable organic solvent, such as diethyl ether. The organic phase and organic extracts are combined, rinsed with brine, dried over anhydrous magnesium sulfate, filtered and concentrated under vacuum to provide the crude ketone (6). The crude material is then purified by flash chromatography on silica gel with a suitable eluent, such as chloroform or methanol/chloroform to provide the purified ketone (6). The purified ketone (6) can be further purified by recrystallization from a suitable solvent system such as chloroform/hexane.

In Scheme C, step C the ketone (6) is reduced to the alcohol of structure (7). For example, the ketone (6) is dissolved in a suitable organic solvent, such as methanol and cooled to about 0° C. The solution is then treated with 1.1 equivalents of a suitable reducing agent, such as sodium borohydride and the reaction is stirred for about one hour. The reaction is then diluted with water, acidified and extracted with a suitable organic solvent, such as chloroform. The combined organic extracts are rinsed with brine, dried over anhydrous magnesium sulfate, filtered and concentrated under vacuum to provide the crude alcohol (7). The crude material is then purified by techniques well known in the art, such as flash chromatography on silica gel with a suitable eluent, such as methanol/chloroform to provide the purified alcohol (7).

In Scheme C, step D the 9-11 epoxide on alcohol (7) opened to provide the compound of formula (Ib). For example, the alcohol (7) dissolved in a suitable organic solvent, such as THF is added to a stirring solution of excess lithium borohydride in anhydrous THF under an atmosphere of nitrogen. To this reaction mixture is added 1.2 equivalents of neat boron trifluoride diethyl etherate. The reaction mixture is then stirred for about 5 hours at room temperature. Water is then carefully added and the reaction is stirred for about 30 additional minutes. The mixture is then poured into water, acidified with 2N aqueous HCl and the mixture is extracted with a suitable organic solvent, such as chloroform. The organic extracts are combined, washed with brine, dried over anhydrous magnesium sulfate, filtered and concentrated under vacuum to provide the crude compound of formula (Ib). The crude material is then purified by techniques well known in the art such as flash chromatography or preparative thin layer chromatography with a suitable eluent, such as methanol/acetone/chloroform to provide the purified compound of formula (Ib).

Alternatively, as described in Scheme C1, the compounds of formula (Ib) can be prepared directly from compound (1), wherein the substituents, unless otherwise indicated, are previously defined. The reagents and starting materials are readily available to one of ordinary skill in the art.

Scheme C1

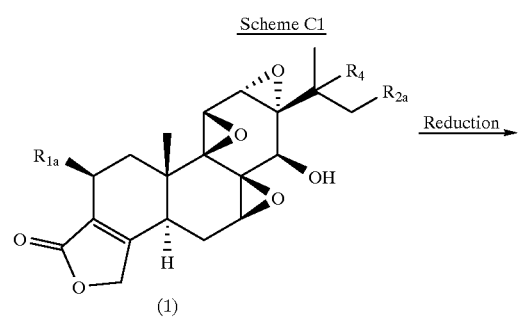

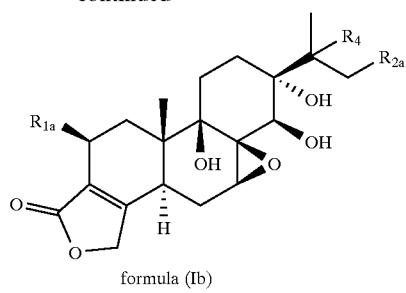

formula (Ib)

In Scheme C1, the compound 1 is reduced directly to provide the compound of formula (Ib). For example, the compound (1) is dissolved in a suitable solvent or solvent mixture, such as anhydrous THF and absolute ethanol, and treated with a suitable reducing agent, such as sodium borohydride. The reaction is heated to about 70° C. for about 5 hours. After cooling, the reaction is quenched with 0.5 N NaOH and the mixture is extracted with a suitable organic solvent, such as ethyl acetate. The organic extracts are combined, washed with brine, dried over anhydrous magnesium sulfate, filtered and concentrated under vacuum to provide the crude compound of formula (Ib). This crude material is then isolated by techniques well known in the art, such a flash chromatography on silica gel with a suitable eluent, such as ethyl acetate/hexane to provide the purified compound of formula (Ib).

The compounds of formulas (I), (II) and (III) can be prepared as described in Scheme D. All substituents, unless otherwise indicated, are previously defined. The reagents and starting materials are readily available to one of ordinary skill in the art.

In Scheme D the compounds of formulas (Ic'), (IIc') and (IIIc') wherein $R_{1a}$ and $R_{2a}$ are each independently hydrogen or —OH, are subjected to standard acylation conditions well known to one of ordinary skill in the art to provide the compounds of formulas (I), (II) and (III). For example, following generally the procedure of J. Swistok, et al., Tetrahedron Letters, 30(38), 5045 (1989), the compound of either formula (Ic'), (IIc') or (IIIc') is dissolved in a suitable organic solvent, such as dimethylformamide. The solution is then treated with one equivalent of a suitable cyclic anhydride, such as succinic anhydride, an equivalent of 4-dimethylaminopyridine (DMAP) and about 1.6 equivalents of pyridine. The reaction is stirred for about 12 hours at room temperature and then concentrated under vacuum. The product is isolated and purified by techniques well known in the art such as extraction techniques and chromatography. For example, the residue is dissolved in a suitable organic solvent, such as methylene chloride, rinsed with water, brine, dried over anhydrous magnesium sulfate, filtered and concentrated under vacuum to provide the crude product. The crude product is then purified by flash chromatography on silica gel with a suitable eluent, such as methanol/chloroform to provide the purified compound of formula (I), (II) or (III).

Alternatively, the compound of either formula (Ic'), (IIc') or (IIIc') can be dissolved in a suitable anhydrous organic solvent, such as pyridine, and then treated with the acid chloride of a suitable monoester of the corresponding suitable diacid. Examples of suitable diacids are succinic acid, glutaric acid, adipic acid, pimelic acid and suberic acid. A suitable monoester of the diacid is an ester that is ultimately de-esterified under mild conditions well known in the art to provide the compounds of formulas (I), (II) or (III). For example, the above solution is treated with one equivalent of the acid chloride of mono-tert-butyl succinate or mono-benzyl succinate, and then stirred for about 2 hours at room temperature. The resulting ester is then isolated and purified Scheme D

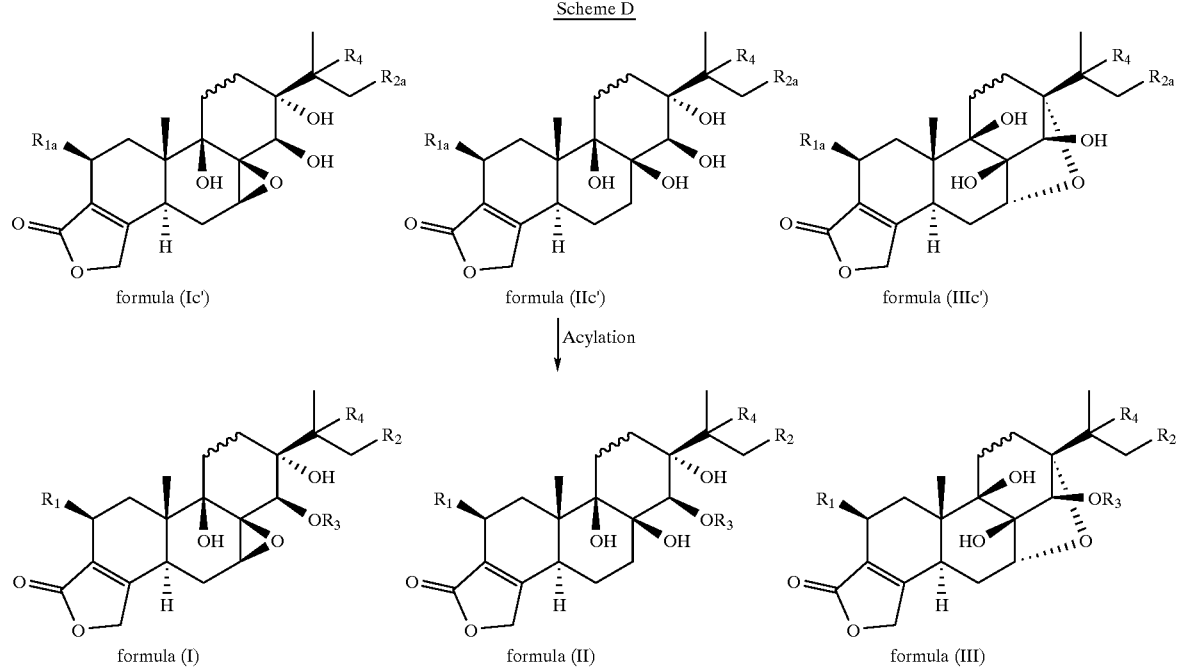

by techniques well known in the art. For example, the solvent is removed under vacuum and the residue is purified by flash chromatography on silica gel with a suitable eluent, such as methanol/chloroform to provide the purified ester. The ester is then converted to the corresponding acid by techniques well known in the art such as acid hydrolysis of the tert-butyl ester or hydrogenation of the benzyl ester as disclosed by T. W. Green, "Protective Groups in Organic Synthesis", John Wiley & Sons Inc, 1981, pages 168–169 and 171–172 respectively to provide the crude compounds of formulas (I), (II) or (III). The crude material is then purified and mixtures separated if necessary by flash chromatography on silica gel with a suitable eluent, such as methanol/chloroform to provide the purified compounds of formulas (I), (II) or (III).

It is readily appreciated by one of ordinary skill in the art that when $R_{1a}$ and/or $R_{2a}$ are —OH in formulas (Ic'), (IIc') and (IIIc') then a mixture of acylated compounds will result in the above procedures wherein acylation can occur either at $R_{1a}$, $R_{2a}$ or the —OH at position 14. It is further understood that the resulting mixture can be separated by techniques well known in the art, such as flash chromatography or high performance liquid chromatography. It is further understood by one of ordinary skill in the art that the compound of formulas (I), (II) or (III) wherein all primary and secondary alcohols have been acylated, requires treatment with at least 1.2 equivalents of the reagent for each such alcohol. For example the compound of formulas (Ic'), (IIc') or (IIIc') must be treated with at least 1.2 equivalents of the suitable cyclic anhydride, at least 1.2 equivalents of DMAP and at least 1.8 equivalents of pyridine, for every primary and secondary alcohol present.

In addition, the compound of either formula (Ic'), (IIc') or (IIIc') can be acylated with an amino acid from Table I, which has been suitably protected, under conditions well known in the art, followed by deprotection of the amino acid portion of the compound to provide the compound of either formula (I), (II) or (III). For example, see P. Joulin, et al., *Tetrahedron Letters*, 28(15), 1661 (1987), D. Grenouillat, et al., *Tetrahedron Letters*, 28(47), 5827 (1987), M. Ueda, et al., *Synthesis,* 908 (1983) and E. Haslam, *Tetrahedron,* 36, 2409 (1980).

It is understood that the functional groups of the constituent amino acids generally must be protected during the coupling reactions to avoid formation of undesired bonds. The protecting groups that can be used, their formation and removal are disclosed by T. W. Greene, "Protective Groups in Organic Chemistry", John Wiley & Sons, New York (1981) and "The Peptides: Analysis, Synthesis, Biology", Vol. 3, Academic Press, New York (1981), the disclosure of which is hereby incorporated by reference.

The a-amino group of each amino acid to be coupled to the primary or secondary alcohol must be protected. Any protecting group known in the art can be used. Examples of which include: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropyl-methoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethyl-silane; and 7) thiol containing types such as phenylthiocarbonyl and dithiasuccinoyl. The preferred a-amino protecting group is either Boc or Fmoc, preferably Boc. Many suitably protected amino acid derivatives are commercially available.

The a-amino protecting group of the added amino acid residue is then cleaved under conditions well known in the art to provide the compound of either formula (I), (II) or (III). For example, when the Boc group is used, the methods of choice are trifluoroacetic acid, neat or in methylene chloride, or HCl in dioxane or ethyl acetate as disclosed in Greene "Protective Groups in Organic Synthesis", John Wiley & Sons, New York (1981), 232–233.

More specifically, the compounds of formulas (Ic), (IIc) or (IIIc) are dissolved in a suitable anhydrous organic solvent, such as methylene choride under an inert atmosphere, such as nitrogen, and treated with an excess of a suitably protected amino acid and about two equivalents of dimethylaminopyridine. Examples of suitably protected amino acids are N-(tert-butoxycarbonyl)-L-alanine, N-(tert-butoxycarbonyl)-L-phenylalanine, N,N'-(ditert-butoxycarbonyl)-lysine, N-(t-butylcarbonyl)omega tert-butoxyl-glutamate and the like. The solution is cooled to 0° C. with stirring and treated with about two equivalents of dicyclohexylcarbodiimide. Then allow the reaction to warm to room temperature and stir for about 3 hours. Then filter the reaction to remove any precipitate and concentrate the filtrate under vacuum. Dissolve the residue in a suitable organic solvent, such as methylene chloride and wash with 0.05 N aqueous HCl, saturated sodium bicarbonate, brine, dry over anhydrous magnesium sulfate, filter and concentrate under vacuum. Purify the residue by flash chromatography on silica gel with a suitable eluent, such as ethyl acetate/hexane to provide the BOC-protected compounds of formulas (I), (II) or (III).

The BOC protecting group is removed under conditions well known in the art. For example, dissolve the BOC protected compounds of formulas (I), (II) or (III) in a suitable organic solvent, such as diethyl ether and treat the solution slowly with 1N trifluoroacetic acid. Allow the reaction to stir for about 1 hour. The trifluoro acetate salt of the compounds of formulas (I), (II) or (III) are then collected by filtration, washed with diethyl ether and dried. The free base of the compounds of formula (I), (II) or (III) can be prepared by dissolving the trifluoroacetate salt in water and treating with at least one equivalent of sodium carbonate. The aqueous solution is then extracted with a suitable organic solvent, such as methylene chloride. The organic extract is then washed with water, brine, dried over anhydrous magnesium sulfate, filtered and concentrated under vacuum to provide the compounds of formulas (I), (II) or (III).

The following examples present typical syntheses as described in Schemes A, B, C, C1 and D. These examples are understood to be illustrative only and are not intended to limit the scope of the present invention in any way. The reagents and starting materials are readily available to one of ordinary skill in the art. As used herein, the following terms have the indicated meanings: "kg" refers to kilograms; "g" refers to grams; "mg" refers to milligrams; "µg" refers to micrograms; "m²/g" refers to square meters per gram and is used as a measurement of particle surface area; "mmol" refers to millimoles; "L" refers to liters; "mL" refers to milliliters; "µL" refers to microliters; "cm" refers to centimeters; "M" refers to molar; "mM" refers to millimolar; "µM" refers to micromolar; "nM" refers to nanomolar; "eq" refers to equivalents; "N" refers to normal; "ppm" refers to parts per million; "δ" refers to parts per million down field from tetramethylsilane; "° C." refers to degrees Celsius; "° F." refers to degrees Fahrenheit; "mm Hg" refers to millimeters of mercury; "kPa" refers to kilopascals; "psi" refers to pounds per square inch; "rpm" refers to revolutions per minute; "bp" refers to boiling point; "mp" refers to melting point; "dec" refers to decomposition; "HPLC" refers to high performance liquid chromatography; "h" refers to hours; "min" refers to minutes; "sec" refers to seconds; "i.p." refers to intraperitoneally; "p.o." refers to orally; "COMC" refers to carboxymethyl cellulose; "THF" refers to tetrahydrofuran; "DMF" refers to N,N-dimethylformamide; "DMSO" refers to dimethyl sulfoxide; "LAH" refers to lithium aluminum hydride; "R$_f$" refers to retention factor; and "R$_t$" refers to retention time.

EXAMPLE 1

Preparation of [5aS-(5aα,5bα,8β,9α,9aR*,10aβ)]-4,5a,5b,8,9,10a,11,11a-octahydro-5b,8,9-trihydroxy-5a-methyl-8-(1-methylethyl)-1H-oxireno[8a,9]phenanthro[1,2-c]furan-3(5)-one

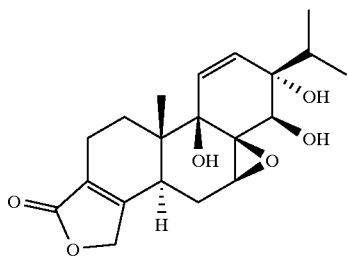

Preparation of intermediate [1bS-(1aR*,1bα,6bβ,7aβ,8aR*,9α,10β,11α,11aβ)]-11-bromo-1b,3,6,6b,7,7a,9,10,11,11a-decahydroxy-10-(1-methylethyl)-1b-methyl-bisoxireno[4b,5:8a,9]phenanthro[1,2-c]furan-4(2H)-one

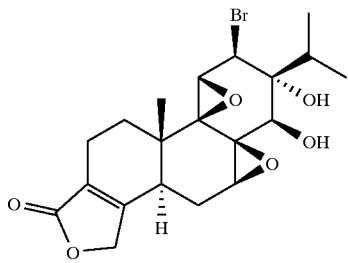

Scheme A, step A; Triptolide (100 mg, 277 mmol, optically active, isolated from natural source) is combined with acetone (30 mL), water (2.5 mL) and 30% aqueous HBr (800 mL), and the reaction mixture is heated at 70° C. for 70 minutes. The reaction mixture is then poured into water (60 mL) and concentrated under vacuum. The remaining phase is then extracted with methylene chloride (3×60 mL), the organic extracts combined, washed with brine (60 mL), dried over anhydrous magnesium sulfate, filtered and concentrated under vacuum to provide a solid (118 mg). This solid material is recrystallized from hexane/methylene chloride to provide the title compound (82 mg, 67%) as white cubes; mp 228° C.; [a]$_D$=−164° (c=0.12, chloroform).
Preparation of Final Title Compound Scheme A, step B; [1bS-(1aR*,1bα,6bβ,7aβ,8aR*,9α,10β,11α,11aβ)]-11bromo-1b,3,6,6b,7,7a,9,10,11,11a-decahydroxy-10-(1-methylethyl)-1b-methyl-bisoxireno[4b,5:8a,9]phenanthro[1,2-c]furan-4(2H)-one (5 mg, 0.011 mmol) is combined with Pd/BaSO$_4$(5 mg) and sodium acetate (1 mg) in ethanol (2 mL), and the reaction mixture is stirred under an atmosphere of hydrogen at room temperature for 3 hours. The reaction mixture is then filtered through diatomaceous earth (CELITE®) and then purified by preparative TLC (20×20 cm, 0.25 mm, 5% methanol/chloroform) to provide the title compound (1.8 mg, 43%). This material is recrystallized from chloroform/hexane to provide the title compound as needles; mp 202–205° C.; [a]$_D$=42.5° (c=0.08, chloroform).

EXAMPLE 2

Preparation of [5aR-(5aα,6α,7β,9aα,9bα)]-3b,4,5,5a,6,7,9a,9b,10,11-decahydro-5a,6,7,9a-tetrahydroxy-9b-methyl-7-(1-methylethyl)-phenanthro[1,2-c]furan-1(3H)-one

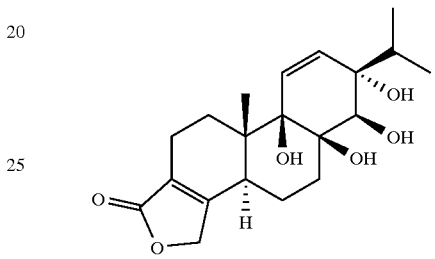

Preparation of intermediate [5aR-(5aα,6α,6aα,7aα,7bβ,8aS*,8bα)]-3,3b,4,5,5a,6,6a,7a,7b,8b,9,10-dodecahydro-5a,6-dihydroxy-6a-(1-methylethyl)-8b-methyl-1H-bisoxireno[4b,5:6,7]phenanthro[1,2-c]furan-1-one

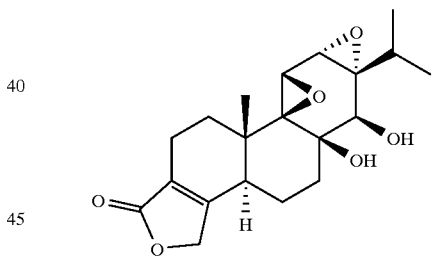

Scheme A, step C; To a stirring solution of triptolide (360 mg, 1 mmol, optically active, isolated from natural source) in dry THF (10 mL) under an atmosphere of nitrogen at room temperature is added sodium cyanoborohydride (360 mg, 6 mmol) followed by dropwise addition of neat boron trifluoride diethyl etherate (150 mL). The resulting solution is stirred at room temperature for 16 hours. The reaction is then quenched by addition of 1N aqueous ammonium chloride (25 mL) and extracted with diethyl ether (3×25 mL). The combined organic extracts are washed with brine (25 mL), dried over anhydrous magnesium sulfate, filtered and concentrated under vacuum to provide a white solid. This white solid is then subjected to the above identical reaction conditions and work-up procedure to provide a white solid (290 mg) which is purified by flash chromatography (chloroform and then 0.5% to 1% methanol/chloroform) to provide the title compound (160 mg, 44%). The title compound is recrystallized from methanol; mp 185–186° C. and [a]$_D$=−32° (c=0.1, chloroform).

Alternative preparation of intermediate [5aR-(5aα, 6α,6aα,7aα,7bβ,8aS*,8bα)]-3,3b,4,5,5a,6,6a,7a,7b, 8b,9,10-dodecahydro-5a,6-dihydroxy-6a-(1-methylethyl-8b-methyl-1H-bisoxireno[4b,5:6,7] phenanthror[1,2-c]furan-1-one Scheme A, step C; To a stirring solution of triptolide (100 mg, optically active, isolated from natural source) at room temperature in dry THF (30 mL) under an atmosphere of nitrogen is added lithium borohydride (264 μL of a 2N solution in THF) followed by addition of neat boron trifluoride diethyl etherate (72 μL). The reaction mixture is allowed to stir for 90 minutes and is then carefully treated 1N HCl (10 mL). After stirring for an additional 10 minutes, the reaction mixture is extracted with methylene chloride (3×20 mL). The organic extracts are combined, washed with 1N sodium bicarbonate (2×20 mL), brine, dried over anhydrous magnesium sulfate, filtered and concentrated under vacuum. The residue is then purified by column chromatography (20% ethyl acetate/hexane) to provide the title compound (76 mg, 76%).

Preparation of Final Title Compound

Scheme A, step D; Dissolve [5aR-(5aα,6α,6aα,7aα,7bβ, 8aS*,8bα)]-3,3b,4,5,5a,6,6a,7a,7b,8b,9,10-dodecahydro-5a, 6-dihydroxy-6a-(1-methylethyl)-8b-methyl-1H-bisoxireno [4b,5:6,7]phenanthro[1,2-c]furan-1-one (10 mg) in chloroform (5 mL) under nitrogen at room temperature and treat with iodo trimethylsilane (5 μL) and triphenylphosphine (4 mg). The solution turns yellow very rapidly and then deep brown. After 10 minutes pour the reaction into water and extract with ethyl acetate (2×10 mL). Combine the organic extracts, wash with 10% sodium thiosulfate, brine, dry over anhydrous magnesium sulfate, filter and concentrate under vacuum. Purify the residue by column chromatography (silica gel, 40% ethyl acetate/hexane) to provide the title compound.

Alternative Synthesis of the Final Title Compound

Preparation of intermediate [1S-(1α,2β,3α,3aβ, 4aR*,4bα,9bβ,11aα)]-3-bromo-1,2,3,3a,4b,5,6,9,9b, 10,11,11a-dodecahydro-1,2,11a-trihydroxy-2-(1-methylethyl)-4b-methyl-7H-oxireno[4b,5] phenanthro[1,2-c]furan-7-one

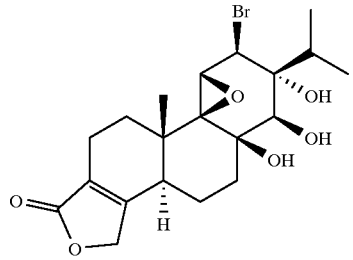

Scheme A, step E; Combine [5aR-(5aα,6α,6aα,7aα,7bβ, 8aS*,8bα)]-3,3b,4,5,5a,6,6a,7a,7b,8b,9,10-dodecahydro-5a, 6-dihydroxy-6a-(1-methylethyl)-8b-methyl-1H-bisoxireno [4b,5:6,7]phenanthro[1,2-c]furan-1-one (33 mg, prepared above) and tetrabutyl ammonium bromide (59 mg) in methylene chloride (10 mL) under an atmosphere of nitrogen. Treat the mixture at room temperature with neat boron trifluoride diethyl etherate (17 mL). After 30 minutes, quench the reaction with water (1 mL), pour into water (10 mL) and extract with methylene chloride (3×10 mL). Combine the organic extracts, wash with water, brine, dry over anhydrous magnesium sulfate, filter and concentrate under vacuum. Purify the residue by column chromatography (silica gel, ethyl acetate/hexane) to provide the title compound (21 mg, 52%).

Preparation of Final Title Compound

Scheme A, step F; Dissolve [1S-(1α,2β,3α,3aβ,4aR*, 4bα,9bβ,11aα)]-3-bromo-1,2,3,3a,4b,5,6,9,9b,10,11,11a-dodecahydro-1,2,11a-trihydroxy-2-(1-methylethyl)-4-methyl-7H-oxireno[4b,5]phenanthro[1,2-c]furan-7-one (14.3 mg) in acetonitrile (10 mL) and add freshly activated zinc powder (10 mg). Then add concentrated HCl (54 mL) dropwise via syringe to the slurry and then stir for 10 minutes. Dilute the reaction mixture with water (10 mL) and remove the acetonitrile under reduced pressure. Extract the residue with ethyl acetate (3×10 mL). Combine the organic extracts, wash with 1N sodium bicarbonate, brine, dry over anhydrous magnesium sulfate, filter and concentrate under vacuum. Purify the residue by flash chromatography (silica gel, ethyl acetate/hexane) to provide the title compound (9.3 mg, 79%)).

EXAMPLE 3

Preparation of [5R-(5α,5aβ,6β,7α,9aβ,9bβ)]-3b,4,5, 5a,6,7,9a,10,11-decahydro-5a,6,9a-trihydroxy-9b-methyl-7-(1-methylethyl)-5,7-epoxyphenanthro[1,2-c]furan-1(3H)-one

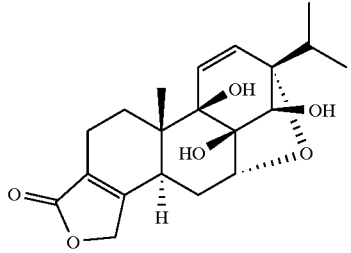

Scheme B, step A; Triptolide (48 mg, 0.133 mmol, optically active, isolated from natural source) is dissolved in acetonitrile (2 mL) and the solution is added dropwise to a stirred mixture of triphenylphosphine (40 mg, 0.153 mmol) and iodine (21.2 mg, 0.084 mmol) in acetonitrile (3 mL) at room temperature under an atmosphere of nitrogen. The reaction mixture is stirred for 10 minutes at room temperature and then at 75° C. for 2 hours. The acetonitrile is then removed under vacuum and water (20 mL) is added. The aqueous suspension is then extracted with ethyl acetate (3×20 mL), the combined organic extracts are washed with 10% aqueous sodium bisulfite (20 mL), brine (20 mL), dried over anhydrous magnesium sulfate, filtered and concentrated under vacuum to provide a yellowish powder (100 mg). This material is then purified by flash chromatography (2% methanol/chloroform) to provide the title compound (38 mg, 80%) as an amorphous powder; $[a]_D = -40°$ (c=0.02, chloroform); IR (NaCl) $n_{max}$ 3460, 2920, 1730, 1660, 1375, 1010, 950, 900, 750 cm$^{-1}$.

EXAMPLE 4

Preparation of [5aS-(5aα,5bα,8β,9α,9aR*, 10aβ)]-4,5a,5b,6,7,8,9,10a,11,11a-decahydro-5b,8,9-trihydroxy-5a-methyl-8-(1-methylethyl)-1H-oxireno[8a,9]phenanthro[1,2-c]furan-3(5H)-one

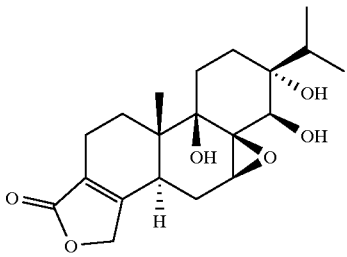

Preparation of intermediate [1bS-(1aR*,1bα,6bβ,7aβ,8aR*,11aβ)]-1b,3,6,6b,7,7a-hexahydro-1b-methyl-10-(1-methylethyl)-bisoxireno[4b,5:8a,9]phenanthro[1,2-c]furan-4,9(2H, 11aH)-dione

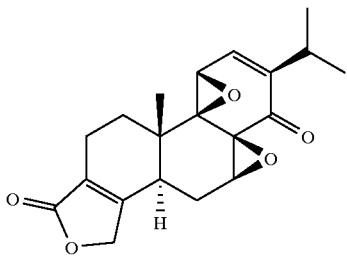

Scheme C, step A; Triptolide (500 mg, 1.38 mmol, optically active, isolated from natural source) is dissolved in dry methylene chloride (140 mL) under an atmosphere of nitrogen. The solution is treated with triethylamine (300 mL, 2.15 mmol) and triethylsilyl triflate (476 mL, 2.1 mmol), and the reaction mixture is stored at 4° C. for 12 hours. The reaction mixture is then warmed to room temperature and additional triethylsilyl triflate (476 mL, 2.1 mmol) is added. The reaction mixture is then stirred for an additional 6 hours at room temperature. The orange to red solution is then poured into water (100 mL) and neutralized with saturated aqueous sodium bicarbonate solution. The phases are separated and the aqueous is extracted with methylene chloride (2×100 mL). The organic phase and organic extracts are then combined, washed with 2N aqueous HCl (100 mL), brine (100 mL), dried over anhydrous magnesium sulfate, filtered and concentrated under vacuum to provide a crystalline solid (880 mg). This material is recrystallized from methylene chloride/methanol to provide the title compound (200 mg). The mother liquor is concentrated under vacuum and the residue purified by flash chromatography (60 g silica gel, chloroform) to provide additional title compound (40 mg) resulting in an overall yield of 50.5% of title compound. The title compound is recrystallized from chloroform/hexane to provide colorless needles; mp 218° C. dec.; [a]$_D$=−277.6° (c=0.3, chloroform);

Preparation of intermediate [1bS-(1aR*,1bα,6bβ,7aβ,8aR*,10β,11aβ)]-1b,3,6,6b,7,7a,11,11a-octahydro-10-hydroxy-1b-methyl-10-(1-methylethyl)-bisoxireno[4b,5:8a,9]phenanthro[1,2-c]furan-4,9(2H, 10H)-dione

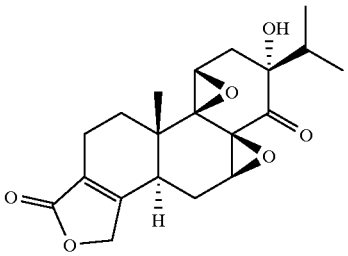

Scheme C, step B; [1bS-(1aR*,1bα,6bβ,7aβ,8aR*,11aβ)]-1b,3,6,6b,7,7a-hexahydro-1b-methyl-10-(1-methylethyl)-bisoxireno[4b,5:8a,9]phenanthro[1,2-c]furan-4,9(2H,11aH)-dione (150 mg) is dissolved in dry THF (40 mL) under an atmosphere of nitrogen and then cooled to −78° C. LS-selectride (450 mL of a 1M solution in THF, 450 mmol) is added dropwise to the solution and the reaction mixture is allowed to stir for 1 hour. The resulting pale yellow reaction mixture is then quenched by addition of CELITE®/MgSO$_4$.7H$_2$O (6 g) and the mixture is allowed to warm to room temperature. The resulting slurry is then filtered through CELITE® and the solids are washed with diethyl ether (2×50 mL). The organic layer is then poured into water (100 mL) and acidified with 2N aqueous HCl. The phases are separated and the aqueous phase is extracted with diethyl ether (2×50 mL). The organic phase and organic extracts are combined, washed with brine (100 mL), dried over anhydrous magnesium sulfate, filtered and concentrated under vacuum to provide a crystalline solid (158 mg). This material is purified by flash chromatography (chloroform then methanol/chloroform) to provide the title compound (30 mg, 18%). The title compound is recrystallized from chloroform/hexane; mp 245–246° C.; [a]$_D$=−125° (c=0.22, chloroform);

Preparation of intermediate [1bS-(1aR*,1bα,6bβ,7aβ,8aR*,9α,10β, 11aβ)]-10-(1-methylethyl)-1b,3,6,6b,7,7a,9,10,11,11a-decahydro-9,10-dihydroxy-1b-methyl-bisoxireno[4b,5:8a,9]phenanthro[1,2-c]furan-4(2H)-one

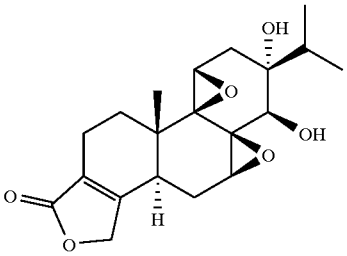

Scheme C, step C; [1bS-(1aR*,1bα,6bβ,7aβ,8aR*,10β,11aβ)]-1b,3,6,6b,7,7a,11,11 a-octahydro-10-hydroxy-1b-methyl-10-(1-methylethyl)-bisoxireno[4b,5:8a,9]phenanthro[1,2-c]furan-4,9(2H, 10H)-dione (18 mg, 50 mmol) is dissolved in methanol (2.5 mL) and cooled to 0° C. To this solution is added sodium borohydride (2 mg, 56 mmol) and the reaction mixture is stirred for 1 hour. Water (10 mL) is then added and the mixture is extracted with chloroform (3×10 mL). The organic layers are combined, washed with brine, dried over anhydrous magnesium sulfate, filtered and concentrated under vacuum. The residue is then purified by preparative TLC on silica gel (3% methanol/chloroform) to provide the title compound (16 mg, 88%). The title compound is recrystallized from chloroform/hexane to provide colorless needles; mp 250–251° C.; $[a]_D=-53.3°$ (c=0.15, chloroform);

Preparation of Final Title Compound

Scheme C, step D; To a stirred solution of lithium borohydride (10 mg, 454 mmol) in dry THF (1 mL) under an atmosphere of nitrogen at room temperature is injected [1bS-(1aR*,1bα,6bβ,7aβ,8aR*,9α,10β,11aβ)]-10-(1-methylethyl)-1b,3,6,6b,7,7a,9,10,11,11a-decahydro-9,10-dihydroxy-1b-methyl-bisoxireno[4b,5:8a,9]phenanthro[1,2-c]furan-4(2H)-one (10 mg dissolved in 1 mL THF, 27 mmol) followed by addition of neat boron trifluoride diethyl etherate (4 mL, 32 mmol). The reaction mixture is then stirred for 5 hours. Water (1 mL) is then carefully injected into the reaction mixture and stirring is continued for an additional 30 minutes. The mixture is then poured into water (10 mL) and acidified with 2N aqueous HCl. The mixture is extracted with chloroform (3×25 mL), the combined organic extracts are washed with brine, dried over anhydrous magnesium sulfate, filtered and concentrated under vacuum. The residue is purified by preparative thin layer chromatography (20×20 mm, 0.2 mm, silica gel, methanol/acetone/chloroform, 3:2:95) to provide the title compound (6 mg, 60%) as an amorphous white solid; $[a]_D=-29°$ (c=0.3, dioxane); IR(KBr)n$_{max}$ 3400, 2900, 1750, 1680, 1440, 1380, 1060, 1000, 960 cm$^{-1}$.

Alternative Preparation of Title Compound

Scheme C1; Triptolide (60 mg, optically active, isolated from natural source) in anhydrous THF (3 mL) and absolute ethanol (6 mL) is treated with sodium borohydride (31.8 mg). The mixture is heated at 70° C. for 5 hours, then allowed to cool, and 0.5 N NaOH (15 mL) is added to the reaction mixture. The resulting suspension is extracted with ethyl acetate (5×20 mL), the organic extracts are combined, washed with brine, dried over anhydrous magnesium sulfate, filtered and concentrated under vacuum. The residue is purified by flash chromatography (silica gel, ethyl acetate/hexane) to provide the title compound (19 mg, 30%) as an amorphous white solid.

EXAMPLE 5

Preparation of [5aR-(5aα,6α,7β,9aα,9bα)]-3b,4,5,5a,6,7,8,9,9a,9b,10,11-dodecahydro-5a,6,7,9a-tetrahydroxy-9b-methyl-7-(1-methylethyl)-phenanthro[1,2-c]furan-1(3H)-one

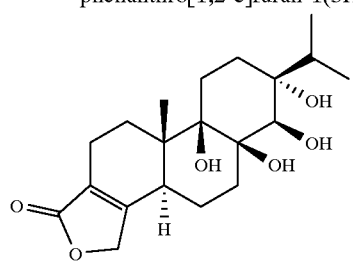

Scheme A, step G; Dissolve [5aR-(5aα,6α,7β,9aα,9bβ)]-3b,4,5,5a,6,7,9a,9b,10,11-decahydro-5a,6,7,9a-tetrahydroxy-9b-methyl-7-(1-methylethyl)-phenanthro[1,2-c]furan-1(3H)-one (10 mg, prepared in example 2) in benzene (5 mL) and treat with Wilkinson's Catalyst (9 mg). Stir the reaction mixture under an atmosphere of hydrogen for 24 hours at room temperature and then filter through a short neutral alumina column. Concentrate the filtrate under vacuum and purify the residue by preparative TLC (silica gel, 2% methanol/chloroform) to provide the title compound.

EXAMPLE 6

Preparation of [5R-(5α,5aβ,6β,7α,9aβ,9bβ)]-3b,4,5,5a,6,7,8,9,9a,9b,10,11-dodecahydro-5a,6,9a-trihydroxy-9b-methyl-7-(1-methylethyl)-5,7-epoxyphenanthro[1,2-c]furan-1(3H)-one

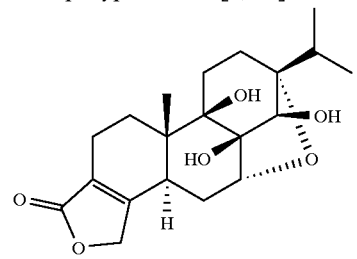

Scheme B, step B; Dissolve [5R-(5α,5aβ,6β,7α,9aβ,9bβ)]-3b,4,5,5a,6,7,9a,10,11-decahydro-5a,6,9a-trihydroxy-9b-methyl-7-(1-methylethyl)-5,7-epoxyphenanthro[1,2-c]furan-1(3H)-one (12 mg, prepared in example 3) in ethanol (5 mL) and treat with Pd on SrCrO$_3$ (4 mg). Stir the reaction under an atmosphere of hydrogen at room temperature for 12 hours, then filter and concentrate the filtrate under vacuum. Purify the residue by flash chromatography (silica gel, 40–50% ethyl acetate/hexane) to provide the title compound.

EXAMPLE 7

Preparation of [4S-(4α,5aα,5bα,8β,9α,9aR*,10aβ,11aβ)]-8-(1-methylethyl)-4,5a,5b,8,9,10a,11,11a-octahydro-4,5b,8,9-tetrahydroxy-5a-methyl-1H-oxireno[8a,9]phenanthro[1,2-c]furan-3(5H)-one

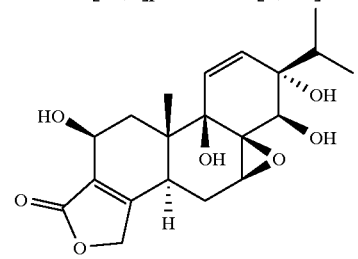

Preparation of intermediate [1bS-(1aR*,1bα,3α,6bβ,7aβ,8aR*,9α,10β,11α,11aβ)]-11-bromo-1b,3,6,6b,7,7a,9,10,11,11a-decahydro-3,9,10-trihydroxy-1b-methyl-10-(1-methylethyl)-bisoxireno[4b,5:8a,9]phenanthro[1,2-c]furan-4(2H)-one

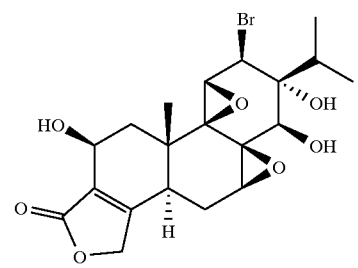

Scheme A, step A; Tripdiolide (104 mg, 277 μmol, optically active, isolated from natural source) is combined with acetone (30 mL), water (2.5 mL) and 30% aqueous HBr (800 μL), and the reaction mixture is heated at 70° C. for 70 minutes. The reaction mixture is then poured into water (60 mL) and concentrated under vacuum. The remaining phase is then extracted with methylene chloride (3×60 mL), the organic extracts combined, washed with brine (60 mL), dried over anhydrous magnesium sulfate, filtered and concentrated under vacuum to provide the title compound.
Preparation of Final Title Compound Scheme A, step B; [1bS-(1aR*,1bα,3a,6bβ,7aβ,8aR*,9α,10β,11α,11aβ)]-11-bromo-1b,3,6,6b,7,7a,9,10,11,11a-decahydro-3,9,10-trihydroxy-1b-methyl-10-(1-methylethyl)-bisoxireno[4b,5:8a,9]phenanthro[1,2-c]furan-4(2H)-one (5 mg) is combined with Pd/BaSO₄ (5 mg) and sodium acetate (1 mg) in ethanol (2 mL), and the reaction mixture is stirred under an atmosphere of hydrogen at room temperature for 3 hours. The reaction mixture is then filtered through diatomaceous earth (CELITE®) and then purified by preparative TLC (20×20 cm, 0.25 mm, 5% methanol/chloroform) to provide the title compound.

EXAMPLE 8

Preparation of [5aR-(5a,6α,7β,9aα,9bα,11α)]-3b,4,5,5a,6,7,9a,9b,10,11-dodecahydro-5a,6,7,9a,11-pentahydroxy-9b-methyl-7-(1-methylethyl)-phenanthro[1,2-c]furan-1-(3H)-one

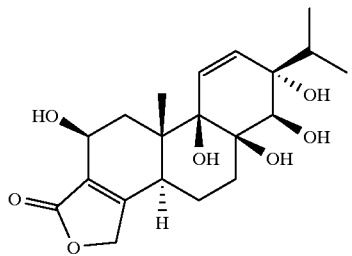

Preparation of intermediate [5aR-(5aα,6α,6aα,7aβ,7bβ,8aS*,8bα,10aα)]-3,3b,4,5,5a,6,6a,7a,7b,8b,9,10-dodecahydro-5a,6,10-trihydroxy-8b-methyl-6a-(1-methylethyl)-1H-bisoxireno[4b,5:6,7]phenanthro[1,2-c]furan-1-one

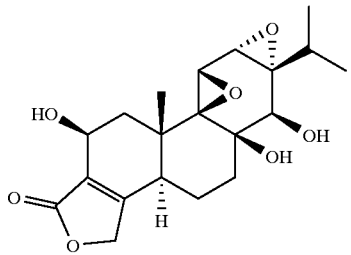

Scheme A, step C; To a stirring solution of tripdiolide (376 mg, 1 mmol, optically active, isolated from natural source) in dry THF (20 mL) under an atmosphere of nitrogen at room temperature is added sodium cyanoborohydride (360 mg, 6 mmol) followed by dropwise addition of neat boron trifluoride diethyl etherate (150 mL). The resulting solution is stirred at room temperature for 16 hours. The reaction is then quenched by addition of 1N aqueous ammonium chloride (25 mL) and extracted with diethyl ether (3×25 mL). The combined organic extracts are washed with brine (25 mL), dried over anhydrous magnesium sulfate, filtered and concentrated under vacuum. The residue is then purified by flash chromatography (chloroform and then 0.5% to 1% methanol/chloroform) to provide the title compound.
Alternative Preparation of Intermediate Scheme A, step C; To a stirring solution of tripdiolide (104 mg) at room temperature in dry THF (30 mL) under an atmosphere of nitrogen is added lithium borohydride (264 μL of a 2N solution in THF) followed by added of neat boron trifluoride diethyl etherate (72 μL). The reaction mixture is allowed to stir for 90 minutes and then carefully treated 1N HCl (10 mL). After stirring for an additional 10 minutes, the reaction mixture is extracted with methylene chloride (3×20 mL). The organic extracts are combined, washed with 1N sodium bicarbonate (2×20 mL), brine, dried over anhydrous magnesium sulfate, filtered and concentrated under vacuum. The residue is then purified by column chromatography (20% ethyl acetate/hexane) to provide the title compound.
Preparation of Final Title Compound Scheme A, step D; Dissolve [5aR-(5aα,6α,6aα,7aα,7bβ,8aS*,8bα,10α)]-3,3b,4,5,5a,6,6a,7a,7b,8b,9,10-dodecahydro-5a,6,10-trihydroxy-8b-methyl-6a-(1-methylethyl)-1H-bisoxireno[4b,5:6,7]phenanthro[1,2-c]furan-1-one (10 mg) in chloroform (5 mL) under nitrogen at room temperature and treat with iodo trimethylsilane (5 mL) and triphenylphosphine (4 mg). The solution turns yellow very rapidly and then deep brown. After 10 minutes pour the reaction into water and extract with ethyl acetate (2×10 mL). Combine the organic extracts, wash with 10% sodium thiosulfate, brine, dry over anhydrous magnesium sulfate, filter and concentrate under vacuum. Purify the residue by column chromatography (silica gel, 1% methanol/chloroform) to provide the title compound.
Alternative Synthesis of the Final Title Compound Preparation of intermediate [1S-(1α,2β,3β,3aβ,4aR*,4bα,6β,9bβ,11aα)]-3-bromo-1,2,3,3a,4b,5,6,9,9b,10,11,11a-dodecahydro-1,2,6,11a-tetrahydroxy-4b-methyl-2-(1-methylethyl)-7H-oxireno[4b,5]phenanthro[1,2-c]furan-7-one

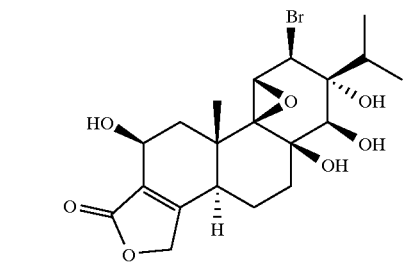

Scheme A, step E; Combine [5aR-(5aα,6α,6aα,7aα,7bβ,8aS*,8bα,10α)]-3,3b,4,5,5a,6,6a,7a,7b,8b,9,10-dodecahydro-5a,6,10-trihydroxy-8b-methyl-6a-(1methylethyl)-1H-bisoxireno[4b,5:6,7]phenanthro[1,2-c]furan-1-one (34.5 mg, prepared above) and tetrabutyl ammonium bromide (59 mg) in methylene chloride (10 mL) under an atmosphere of nitrogen. Treat the mixture at room temperature with neat boron trifluoride diethyl etherate (17 mL). After 30 minutes, quench the reaction with water (1 mL), pour into water (10 mL) and extract with methylene chloride (3×10 mL). Combine the organic extracts, wash with water, brine, dry over anhydrous magnesium sulfate, filter and concentrate under vacuum. Purify the residue by column chromatography (silica gel, ethyl acetate/hexane) to provide the title compound.
Preparation of Final Title Compound Scheme A, step F; Dissolve [1S-(1β,2β,3α,3aβ,4aR*,4bα,6α,9bβ,11aα)]-3-bromo-1,2,3,3a,4b,5,6,9,9b,10,11, 11a-dodecahydro-1,2,6,11a-tetrahydroxy-4b-methyl-2-(1-methylethyl)-7H-oxireno[4b,5]phenanthro[1,2-c]furan-7-one (14.9 mg) in acetonitrile (10 mL) and add freshly activated zinc powder (10 mg). Then add concentrated HCl (54 mL) dropwise via syringe to the slurry and then stir for 10 minutes. Dilute the reaction mixture with water (10 mL) and remove the acetonitrile under reduced pressure. Extract the residue with ethyl acetate (3×10 mL). Combine the organic extracts, wash with 1N sodium bicarbonate, brine, dry over anhydrous magnesium sulfate, filter and concentrate under vacuum. Purify the residue by flash chromatography (silica gel, ethyl acetate/hexane) to provide the title compound.

EXAMPLE 9

Preparation of [3bS-(3bα,5α,5aβ,6β,7α,9aβ,9bβ,11β)]-3b,4,5,5a,6,7,9a,9b,10,11-decahydro-5a,6,9a,11-tetrahydroxy-9b-methyl-7-(1-methylethyl)-5,7-epoxyphenanthro[1,2-c]furan-1(3H)-one

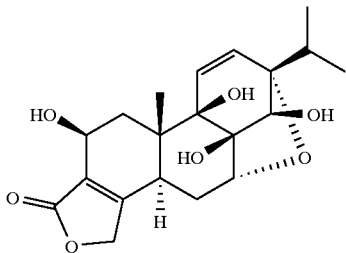

Scheme B, step A; Tripdiolide (50 mg,) is dissolved in acetonitrile (2 mL) and the solution is added dropwise to a stirred mixture of triphenylphosphine (40 mg, 0.153 mmol) and iodine (21.2 mg, 0.084 mmol) in acetonitrile (3 mL) at room temperature under an atmosphere of nitrogen. The reaction mixture is stirred for 10 minutes at room temperature and then at 75° C. for 2 hours. The acetonitrile is then removed under vacuum and water (20 mL) is added. The aqueous suspension is then extracted with ethyl acetate (3×20 mL), the combined organic extracts are washed with 10% aqueous sodium bisulfite (20 mL), brine (20 mL), dried over anhydrous magnesium sulfate, filtered and concentrated under vacuum. This material is then purified by flash chromatography (2% methanol/chloroform) to provide the title compound.

EXAMPLE 10

Preparation of [5aS-(5aα,5bα,8β,9α,9aR*,10aβ,11aβ)]-4,5a,5b,8,9,10a,11,11a-octahydro-5b,8,9-trihydroxy-8-(1-hydroxy-1-methylethyl)-5a-methyl-1H-oxireno[8a,9]phenanthro[1,2-c]furan-3(5H)-one

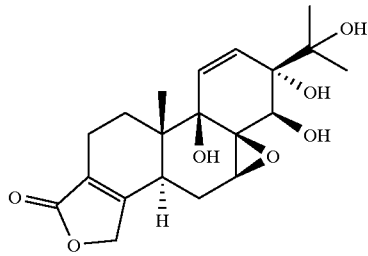

Preparation of intermediate [1bS-(1aR*,1bβ,6bβ,7aβ,8aR*,9α,10β,11α,11aβ]-11-bromo-1b,3,6,6b,7,7a,9,10,11,11a-decahydro-9,10-dihydroxy-10-(1-hydroxy-1-methylethyl)-1b-methyl-bisoxireno[4b,5:8a,9]phenanthro[1,2-c]furan-4(2H)-one

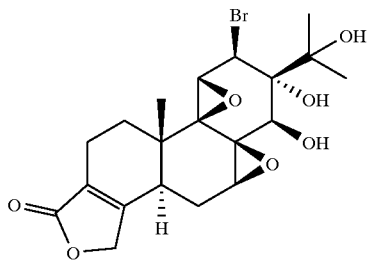

Scheme A, step A; In a manner analogous to the procedure described in example 1, the above intermediate is prepared from triptolidenol.
Preparation of Final Title Compound
Scheme A, step B; In a manner analogous to the procedure described in example 1, the final title compound is prepared from the above prepared intermediate.

EXAMPLE 11

Preparation of [5aR-(5aα,6α,7β,9aα,9bα)-3b,4,5,5a,6,7,9a,9b,10,11-decahydro-5a,6,7,9a-tetrahydroxy-7-(1-hydroxy-1-methylethyl)-9b-methyl-phenanthro[1,2-c]furan-1(3H)-one

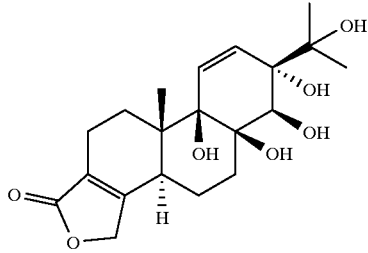

Preparation of intermediate [5aR-(5aα,6α,6aα,7aα,7bβ,8aS*,8bα)]-3,3b,4,5,5a,6,6a,7a,7b,8b,9,10-dodecahydro-5a,6-dihydroxy-6a-(1-hydroxy-1-methylethyl)-8b-methyl-1H-bisoxireno[4b,5:6,7]phenanthro[1,2-c]furan-1-one

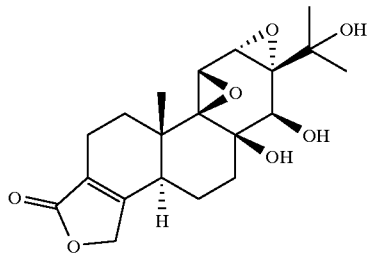

Scheme A, step C; In a manner analogous to the procedure described in example 2 the intermediate is prepared from triptolidinol.

Preparation of Final Title Compound

Scheme A, step D; In a manner analogous to the procedure described in example 2, the final title compound is prepared from the above prepared intermediate.

EXAMPLE 12

Preparation of [3bS-(3bα,5α,5aβ,6β,7α,9aβ,9bβ)]-3b,4,5,5a,6,7,9a,9b,10,11-decahydro-5a,6,9a-trihydroxy-7-(1-hydroxy-1-methylethyl)-9b-methyl-5,7-epoxyphenanthro[1,2-c]furan-1(3H)-one

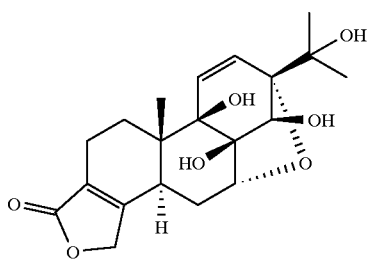

Scheme B, step A; In a manner analogous to the procedure described in example 3, the title compound is prepared from triptolidinol.

EXAMPLE 13

Preparation of [5aS-(5aα,5bα,8β,9α,9aR*,10aβ)]-4,5a,5b,8,9,10a,11,11a-octahydro-5b,8,9-trihydroxy-5a-methyl-8-(2-hydroxy-1-methylethyl)-1H-oxireno[8a,9]phenanthro[1,2-c]furan-3(5H)-one

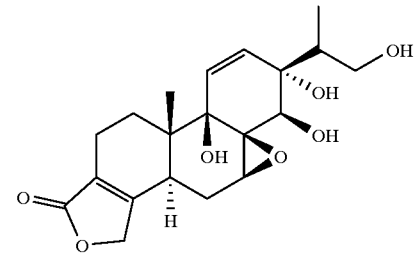

Preparation of intermediate [1bS-(1aR*,1bα,6bβ,7aβ,8aR*,9α,10β,11α,11aβ)]-11-bromo-10-(2-hydroxy-1-methylethyl)-1b,3,6,6b,7,7a,9,10,11,11a-decahydro-9,10-dihydroxy-1b-methyl-bisoxireno[4b,5:8a,9]phenanthro[1,2-c]furan-4(2H)-one

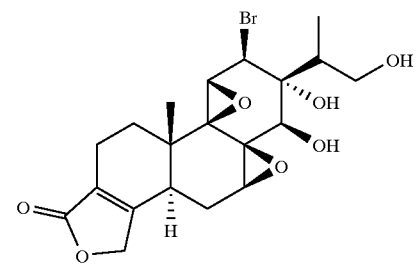

Scheme A, step A; In a manner analogous to the procedure described in example 1, the above intermediate is prepared from 16-hydroxy-triptolide.
Preparation of Final Title Compound
Scheme A, step B; In a manner analogous to the procedure described in example 1, the final title compound is prepared from the above prepared intermediate.

EXAMPLE 14

Preparation of [5aR-(5aα,6α,7β,9aα,9bα)]-3b,4,5,5a,6,7,9a,9b,10,11-decahydro-5a,6,7,9a-tetrahydroxy-7-(2-hydroxy-1-methylethyl)-9b-methyl-phenanthro[1,2-c]furan-1(3H)-one

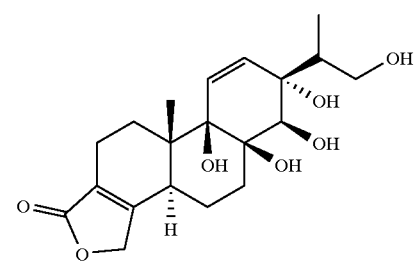

Preparation of intermediate [5aR-(5aα,6α,6aα,7aα,7bβ,8aS*,8bα)]-3,3b,4,5,5a,6,6a,7a,7b,8b,9,10-dodecahydro-5a,6-dihydroxy-6a-(2-hydroxy-1-methylethyl)-8b-methyl-1H-bisoxireno[4b,5:6,7]phenanthro[1,2-c]furan-1-one

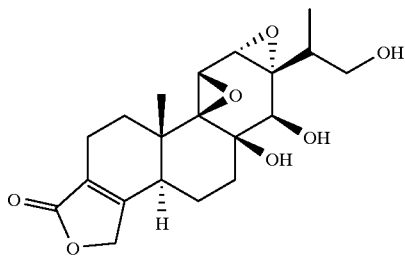

Scheme A, step C; In a manner analogous to the procedure described in example 2 the intermediate is prepared from 16-hydroxy-triptolide.

Preparation of Final Title Compound

Scheme A, step D; In a manner analogous to the procedure described in example 2, the final title compound is prepared from the above prepared intermediate.

EXAMPLE 15

Preparation of [5R-(5α,5aβ,6β,7α,9aβ,9bβ)-3b,4,5,5a,6,7,a,10,11-decahydro-5a,6,9a-trihydroxy-9b-methyl-7-(2-hydroxy-1-methylethyl)-5,7-epoxyphenanthro[1,2-c]furan-1(3H)-one

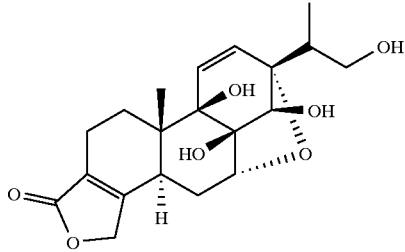

Scheme B, step A; In a manner analogous to the procedure described in example 3, the title compound is prepared from 16-hydroxy-triptolide.

EXAMPLE 16

Preparation of [5aS-(5aα,5bα,8β,9α,9aS*,10aβ,11aβ)]-mono[3,4,5,5a,5b,8,9,10a,11,11a-decahydro-5b,8-dihydroxy-5a-methyl-8-(1-methylethyl)-3-oxo-1H-oxireno[8a,9]phenanthro[1,2-c]furan-9-yl]ester, butanedioic acid

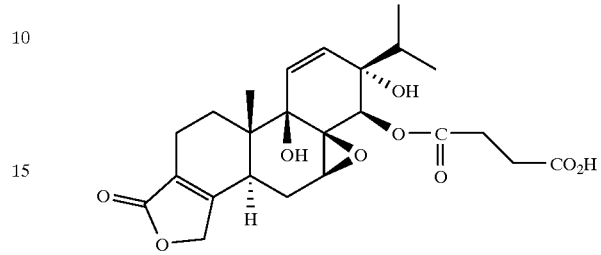

Scheme D; Combine [5aS-(5aα,5bα,8β,9α,9aR*,10aβ)]-4,5a,5b,8,9,10a,11,11a-octahydro-5b,8,9-trihydroxy-5a-methyl-8-(1-methylethyl)-1H-oxireno[8a,9]phenanthro[1,2-c]furan-3(5H)-one (1 mmol, prepared in example 1), succinic anhydride (1.1 mmol), 4-dimethylaminopyridine (1.1 mmol) and pyridine (0.10 mL) in DMF (3 mL). Stir the reaction mixture at room temperature for 24 hours and then concentrate under vacuum. Add water and then make slightly acidic with addition of 1N HCl. Extract the aqueous with methylene chloride (3×5 mL), combine the organic extracts, dry over anhydrous magnesium sulfate, filter and concentrate under vacuum. Purify the residue by flash chromatography on silica gel (1% to 5% methanol/chloroform) to provide the title compound.

EXAMPLE 17

Preparation of [3bS-(3bα,5aβ,6β,7α,9aβ,9bβ)]-mono[1,3,3b,4,5,5a,6,7,9a,10,11-dodecahydro-5a,7,9a-trihydroxy-9b-methyl-7-(1-methylethyl)-1-oxophenanthro[1,2-c]furan-6-yl ]ester, butanedioic acid

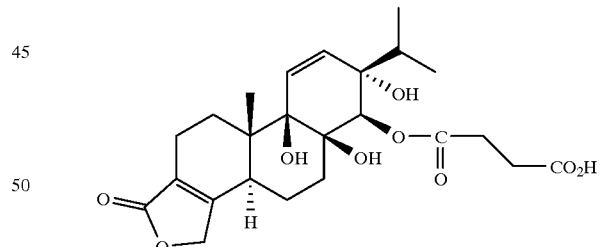

Scheme D; Combine [5aR-(5aα,6α,7β,9aα,9bα)]-3b,4,5,5a,6,7,9a,9b,10,11-decahydro-5a,6,7,9a-tetrahydroxy-9b-methyl-7-(1-methylethyl)-phenanthro[1,2-c]furan-(3H)-one (1 mmol, prepared in example 2), succinic anhydride (1.1 mmol), 4-dimethylaminopyridine (1.1 mmol) and pyridine (0.10 mL) in DMF (3 mL). Stir the reaction mixture at room temperature for 24 hours and then concentrate under vacuum. Add water and then make slightly acidic with addition of 1N HCl. Extract the aqueous with methylene chloride (3×5 mL), combine the organic extracts, dry over anhydrous magnesium sulfate, filter and concentrate under vacuum. Purify the residue by flash chromatography on silica gel (1% to 5% methanol/chloroform) to provide the title compound.

EXAMPLE 18

Preparation of [3bS-(3bα,5α,5aβ,6β,7α,9bβ)]-mono [1,3,3b,4,5,5a,6,7,9a,9b,10,11-dodecahydro-5a,9a-dihydroxy-9b-methyl-7-(1-methylethyl)-1-oxo-5,7-epoxyphenanthro]1,2-c]furan-6-yl]ester, butanedioic acid

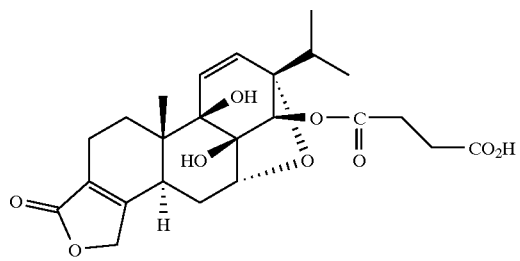

Scheme D; Combine [5R-(5α,5aβ,6β,7α,9aβ,9bβ)]3b,4,5,5a,6,7,9a,10,11-decahydro-5a,6,9a-trihydroxy-9b-methyl-7-(1-methylethyl)-5,7-epoxyphenanthro[1,2-c]furan-1(3H)-one (1 mmol, prepared in example 3), succinic anhydride (1.1 mmol), 4-dimethylaminopyridine (1.1 mmol) and pyridine (0.10 mL) in DMF (3 mL). Stir the reaction mixture at room temperature for 24 hours and then concentrate under vacuum. Add water and then make slightly acidic with addition of 1N HCl. Extract the aqueous with methylene chloride (3×5 mL), combine the organic extracts, dry over anhydrous magnesium sulfate, filter and concentrate under vacuum. Purify the residue by flash chromatography on silica gel (1% to 5% methanol/chloroform) to provide the title compound.

EXAMPLE 19

Preparation of [5aS-(5aα,5bβ,8β,9α,9aS*,10aβ,11aβ)]-mono-[3,4,5,5a,8,9,10a,11,11a-decahydro-5b,8-dihydroxy-5a-methyl-8-(1-methylethyl)-3-oxo-1H-oxireno[8a,9]phenanthro[1,2-c]furan-9-yl]ester, pentanedioic acid

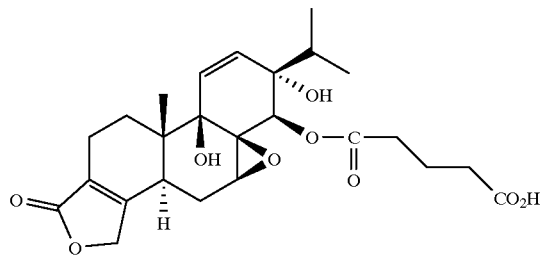

Scheme D; In a manner analogous to the procedure described in example 16, the title compound is prepared from glutaric anhydride and the title compound prepared in example 1.

EXAMPLE 20

Preparation of [4S-(4α,5aα,5bα,8β,9α,9aS*,10aβ,11aβ]-3,4,5,5a,5b,8,9,10a,11,11a-decahydro-5b,8-dihydroxy-5a-methyl-8-(1-methylethyl)-3-oxo-1H-oxireno[8a,9]phenanthro[1,2-c]furan-4,9-diyl]ester, butanedioic acid

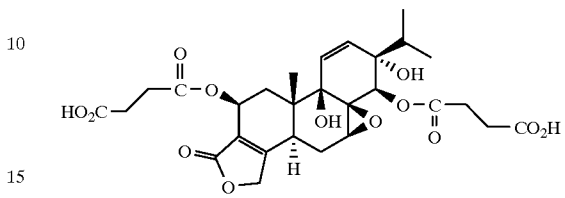

Scheme D; Combine (1 mmol, prepared in example 7), succinic anhydride (2.2 mmol), 4-dimethylaminopyridine (2.2 mmol) and pyridine (0.20 mL) in DMF (3 mL). Stir the reaction mixture at room temperature for 24 hours and then concentrate under vacuum. Add water and then make slightly acidic with addition of 1N HCl. Extract the aqueous with methylene chloride (3×5 mL), combine the organic extracts, dry over anhydrous magnesium sulfate, filter and concentrate under vacuum. Purify the residue by flash chromatography on silica gel (1% to 5% methanol/chloroform) to provide the title compound.

EXAMPLE 21

Preparation of [3bS-(3bα,5aβ,6β,7α,9aβ,9bβ]-1,3,3b,4,5,5a,6,7,9a,9b,10,11-dodecahydro-5a,7,9a-trihydroxy-9b-methyl-7-(1-methylethyl)-1-oxophenanthro[1,2-c]furan-6-yl ester, L-alanine, trifluoroacetate

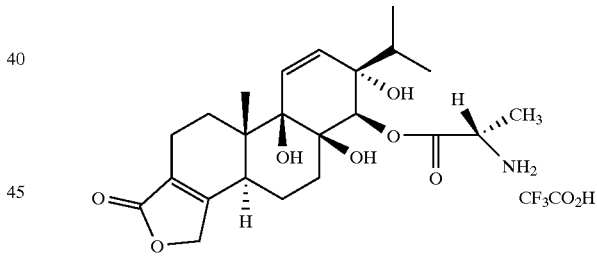

Scheme D; Combine [5aR-(5aα,6α,7β,9aα,9bα)]-3b,4,5,5a,6,7,9a,9b,10,11-decahydro-5a,6,7,9a-tetrahydroxy-9b-methyl-7-(1-methylethyl)-phenanthro[1,2-c]furan-1(3H)-one (36 mg, 0.1 mmol, prepared in example 2) with N-(tert-butoxycarbonyl)-L-alanine (21 mg, 0.11 mmol) and dimethylaminopyridine (23 µL, 0.2 mmol) in anhydrous methylene chloride (15 mL) under an atmosphere of nitrogen. Cool the solution to 0° C. and add dicyclohexylcarbodiimide (40 mg, 0.2 mmol). Warm the reaction to room temperature and stir for 4 hours. Then filter the reaction and concentrate the filtrate under vacuum. Dissolve the residue in methylene chloride (20 mL) and wash with 0.5 N HCl (20 mL), saturated sodium bicarbonate (20 mL) and brine (20 mL). Dry the organic over anhydrous magnesium sulfate, filter and concentrate the filtrate under vacuum. Purify the residue by flash chromatography (silica gel, ethyl acetate/hexane) to provide the purified BOC-protected title compound. Dissolve the BOC-protected title compound in diethyl ether (15 mL) and treat slowly with 1N trifluoroacetic acid (2 mL). Stir the reaction for 1 hour and filter is the reaction to collect the solid. Wash the solid with diethyl ether and dry under vacuum to provide the title compound.

EXAMPLE 22

Preparation of [3bS-(3bα,5aβ,6β,7α,9aβ,9bβ)]1,3,3b,4,5,5a,6,7,9a,10,11-dodecahydro-5a,7,9a-trihydroxy-9b-methyl-7-(1-methylethyl)-1-oxophenanthro[1,2-c]furan-6-yl ester, L-phenylalanine, trifluoroacetate

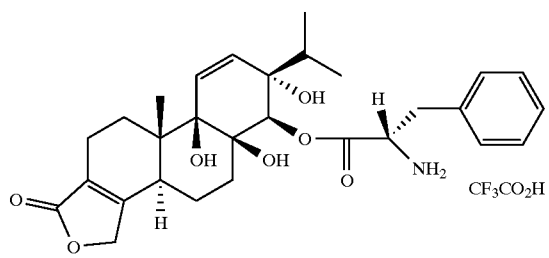

Scheme D; Combine [5aR-(5aα,6α,7β,9aα,9bα)]-3b,4,5,5a,6,7,9a,9b,10,11-decahydro-5a,7,9a-tetrahydroxy-9b-methyl-7-(1-methylethyl)-phenanthro[1,2-c]furan-1(3H)-one (36 mg, 0.1 mmol, prepared in example 2) with N-(tert-butoxycarbonyl)-L-phenylalanine (29.1 mg, 0.11 mmol) and dimethylaminopyridine (23 μL, 0.2 mmol) in anhydrous methylene chloride (15 mL) under an atmosphere of nitrogen. Cool the solution to 0° C. and add dicyclohexylcarbodiimide (40 mg, 0.2 mmol). Warm the reaction to room temperature and stir for 4 hours. Then filter the reaction and concentrate the filtrate under vacuum. Dissolve the residue in methylene chloride (20 mL) and wash with 0.5 N HCl (20 mL), saturated sodium bicarbonate (20 mL) and brine (20 mL). Dry the organic over anhydrous magnesium sulfate, filter and concentrate the filtrate under vacuum. Purify the residue by flash chromatography (silica gel, ethyl acetate/hexane) to provide the purified BOC-protected title compound. Dissolve the BOC-protected title compound in diethyl ether (15 mL) and treat slowly with 1N trifluoroacetic acid (2 mL). Stir the reaction for 1 hour and filter the reaction to collect the solid. Wash the solid with diethyl ether and dry under vacuum to provide the title compound.

The following examples are provided in order to illustrate the method of use of the present invention. This example is intended to be illustrative only and is not to be construed so as to limit the scope of the invention in any way.

EXAMPLE 23

Interleukin-2 Assays

Jurkat E6-1 cell line (ATCC), a human leukemic T cell line or lymphocytes prepared from fresh human blood, are grown in complete culture medium consisting of RPMI-1640 (Mediatech) supplemented with 10% v/v fetal bovine serum (HyClone, Logen, Vt.), penicillin (100 units/mL), streptomycin (200 mg/mL), and 2 mM L-glutamine (GIBCO, Grand Island, N.Y.). The cells are grown to a concentration of between 1.2 to $1.8 \times 10^6$ cells/mL before use. The cells are then centrifuged at low speed and resuspended to a concentration of $1.25 \times 10^6$ cells/mL in fresh medium.

The compounds to be tested are dissolved in DMSO, and water is added to make a 50% DMSO/water solution. The compounds are then diluted in sterile water such that the DMSO concentrations are less then 0.05%. The cells at a concentration of $1.25 \times 10^6$ cells/mL are stimulated with phytohemagglutinin 10 μg/mL (PHA) and $10^{-8}$ M phorbol ester (12-O-tetradecanoylphorbol 13-acetate: TPA), (Sigma, St. Louis, Mo.). The compounds are then added and the cells are plated in flat-bottom tissue culture plates (Falcon, Lincoln Park, N.J.), with 250,000 cells/well. Plates are then incubated at 37° C. under an atmosphere of 5% $CO_2$.

After incubation (16–24 hours), the cells are assayed for IL-2 production and cell viability (MTT). IL-2 production is assayed utilizing a solid phase ELISA immunoassay, sold in kit form by R&D Systems, Inc., Minneapolis, Minn.

EXAMPLE 24

Cell Viability

Cell viability is measured by the use of a mitochondrial enzyme assay. After removal of the supernatant for the IL-2 assay, Cell Titer 96 (a commercial solution of MTT available from Promega, Madison, Wis.) is added to the plates and incubated for 4 hours at 37° C. A solubilization solution is then added and incubated overnight. The plates are then read on an ELISA plate reader at a wavelength of 570 nm. Table II presents the results for the lnterleukin-2 assay, the cell viability assay and the ratio of cell viability/IL-2 inhibition.

TABLE II

| Compound | $IC_{50}$/IL-2 (ng/mL) | $IC_{50}$/MTT (ng/mL) | MTT/IL-2 |
|---|---|---|---|
| Triptolide | 1 to 3 | 5 | 2 to 4 |
| Example 1 | 1,000 | >>1,000 | — |
| Example 2 | 14 | 90 | 6.4 |
| Example 3 | 500 | >>1,000 | — |

EXAMPLE 25

Anti-inflammatory Activity in the Rat Model of Adjuvant-induced Arthritis

Following generally the procedure of Pearson and Wood, Arth. Rheum., 2, 44 (1959), the anti-inflammatory activity of the following compounds was determined in a rat model of adjuvant-induced arthritis. Male Wistar-Lewis rats (Mollegaard, Breeding Centre Ltd, BIBY, DK 4623 LI, SKENSVED, P.P. Box 28, DK) with a body weight between 160 g and 200 g are used. Freund's adjuvant (0.1 mL, 6 mg Mycobacterium smegmatis suspension per mL in heavy white paraffin oil, Merck/Darmstadt) was injected into the base of the tail. Between day 10 and day 14 of the test, immunopathological processes lead to chronic inflammation, especially in the form of arthritic and periarthritic symptoms in all parts of the body. The animals received standardized food Altromin-R (Altrogge, Lage) and had free access to water. The compounds were administered i.p. (suspension in a carboxymethyl cellulose solution in an injection volume of 0.5 mL/100 g body weight) on 12 consecutive days, starting with the day of the adjuvant injection. On day 1 and day 18 of the study, the volume to of both hind paws and the body weight were recorded, and in addition on day 18 the arthritis index. Cyclosporin A and Prednisolone were used as standard compounds. The results of the above test are presented in table III. In addition, table IV presents the percent change in body weight (weight gain) between day 1 and day 21 of the above test.

TABLE III

| Compound | Dose mg/kg/day i,p, | % Inhibition |
|---|---|---|
| Example 2 | 2 | 83 |
| Example 2 | 4 | 72 |
| Triptolide | 0.2 | 70 |
| Triptolide | 0.4 | 85 |
| Triptolide | 0.8 | 76 |
| Cyclosporin A | 10 | 100 |
| Prednisolone | 15 | 100 |

TABLE IV

| Compound | Dose mg/kg/day i,p, | % Change in Body Weight |
|---|---|---|
| Example 2 | 2 | 18.3 |
| Example 2 | 4 | 24.1 |
| Triptolide | 0.2 | 17.2 |
| Triptolide | 0.4 | 22.0 |
| Triptolide | 0.8 | 18.0 |
| Cyclosporin A | 10 | 27.2 |
| Prednisolone | 15 | 14.2 |
| Adjuvant-arthritis Control, CMC | 5 mL | 17.9 |
| Normal non-arthritic animals | — | 32 |

The present invention provides a method of treating a patient suffering from an autoimmune disease comprising administering to said patient an effective amount of a compound of either formula (I), (II) or (III). The term "autoimmune disease" refers to those disease states and conditions wherein the immune response of the patient is directed against the patient's own constituents resulting in an undesirable and often terribly debilitating condition. Included within the scope of autoimmune disease is ARDS, inflammatory bowel disease including ulcerative colitis and Crohn's disease, rheumatoid arthritis, diabetes mellitus type I, Kawasaki disease, multiple sclerosis, familial Mediterranean fever, psoriasis and lupus. Patients suffering from autoimmune diseases are in need of treatment with an antiinflammatory agent such as a compound of formulas (I), (II) or (III). In addition, patients suffering from allograft rejection and Graft-versus-host disease are also in need of treatment with an antiinflammatory agent such as a compound of formulas (I), (II) or (III). As such, treatment of patients suffering from these diseases by administration of a compound of formulas (I), (II) or (III) will be particularly effective in preventing further deterioration or worsening of the patient's condition. Treatment of a patient at an early stage of an autoimmune disease would be particularly effective in preventing further deterioration of the disease state into a more serious condition. The autoimmune diseases for which treatment with a compound of formulas (I), (II) or (III) will be particularly preferred are rheumatoid arthritis, juvenile arthritis, systemic lupus erythematosus and psoriasis.

As used herein, the term "patient" refers to a warm-blooded animal such as a mammal which is suffering from, or is in danger of suffering from, an acute or chronic inflammation, cellular injury or cell death associated with an immunological based disease, such as an autoimmune disease. It is understood that humans, dogs, guinea pigs, mice and rats are included within the scope of the term "patient".

Administration of a compound of formulas (I), (II) or (III) to a patient results in an immunosuppressive or antiinflammatory effect in the patient. Based on standard clinical and laboratory tests and procedures, an attending diagnostician, as a person skilled in the art, can readily identify those patients who are in need of treatment with an immunosuppressive or antiinflammatory agent such as a compound of formulas (I), (II) or (III).

An effective amount of a compound of formulas (I), (II) or (III) is that amount which is effective, upon single or multiple dose administration to a patient, in providing an immunosuppressive or antiinflammatory effect.

An effective amount of a compound of formulas (I), (II) or (III) can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective amount of a compound of formulas (I), (II) or (III) is expected to vary from about 0.1 milligram per kilogram of body weight per day (mg/kg/day) to about 50 mg/kg/day. Preferred amounts are expected to vary from about 0.2 to about 25 mg/kg/day, with about 1 to about 10 mg/kg/day being preferred.

In effecting treatment of a patient afflicted with a disease state described above, a compound of formulas (I), (II) or (III) can be administered in any form or mode which makes the compound bioavailable in effective amounts, including oral and parenteral routes. For example, compounds of formulas (I), (II) or (III) can be administered orally, subcutaneously, intramuscularly, intravenously, transdermally, intranasally, rectally, and the like. Oral administration and intravenous administration are generally preferred. One skilled in the art of preparing formulations can readily select the proper form and mode of administration depending upon the particular characteristics of the compound selected the disease state to be treated, the stage of the disease, and other relevant circumstances.

The compounds of formulas (I), (II) or (III) can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formulas (I), (II) or (III) in admixture or otherwise in association with one or more inert carriers. These compositions are useful, for example, as assay standards, as convenient means of making bulk shipments, or as pharmaceutical compositions. An assayable amount of a compound of formulas (I), (II) or (III) is an amount which is readily measurable by standard assay procedures and techniques as are well known and appreciated by those skilled in the art. Assayable amounts of a compound of formulas (I), (II) or (III) will generally vary from about 0.001% to about 75% of the composition by weight. Inert carriers can be any material which does not degrade or otherwise covalently react with a compound of formulas (I), (II) or (III). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of formula (I), (II) or (III) in admixture or otherwise in association with one or more pharmaceutically acceptable carriers or excipients. The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use, including topical use, and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, including topical administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (I) wherein $R_1$, $R_2$, $R_3$ and $R_4$ are hydrogen, and ⌇⌇ is a double bond or single bond; $R_1$ is OH, $R_2$, $R_3$ and $R_4$ are hydrogen and ⌇⌇ is a double bond or single bond; $R_2$ is OH, $R_1$, $R_3$ and $R_4$ are hydrogen and ⌇⌇ is a double bond or single bond; and $R_1$, $R_2$ and $R_4$ are hydrogen and $R_3$ is $C(=O)(CH_2)_3CO_2H$;

and for compounds of formula (II) wherein $R_1$, $R_2$, $R_3$ and $R_4$ are hydrogen, and ⌇⌇ is a double bond or single bond; $R_1$ is OH, $R_2$, $R_3$ and $R_4$ are hydrogen and ⌇⌇ is a double bond or single bond; $R_2$ is OH, $R_1$, $R_3$ and $R_4$ are hydrogen and ⌇⌇ is a double bond or single bond; and $R_1$, $R_2$ and $R_4$ are hydrogen and $R_3$ is $C(=O)(CH_2)_2CO_2H$ or $C(=O)(CH_2)_3CO_2H$, with most preferred being $R_1$, $R_2$, $R_3$ and $R_4$, and ⌇⌇ is a double bond or single bond;

and for compounds of formula (III) wherein $R_1$, $R_2$, $R_3$ and $R_4$ are hydrogen, and ⌇⌇ is a double bond or single bond; $R_1$ is OH, $R_2$, $R_3$ and $R_4$ are hydrogen and ⌇⌇ is a double bond or single bond; $R_2$ is OH, $R_1$, $R_3$ and $R_4$ are hydrogen and ⌇⌇ is a double bond or single bond; and $R_1$, $R_2$ and $R_4$ are hydrogen and $R_3$ is $C(=O)(CH_2)_2CO_2H$ or $C(=O)(CH_2)_3CO_2H$, with most preferred being $R_1$, $R_2$, $R_3$ and $R_4$, and ⌇⌇ is a double bond or single bond. Also, for substituents $R_3$ and $R_5$, each independently, in compounds of formulas (I), (II) and (III), the preferred suitable amino acids are Ala, Gln, Lys, Arg, and Phe, with Ala, Gln and Lys being most preferred.

What is claimed is:

1. A compound of the formula:

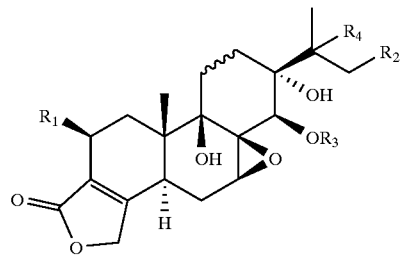

wherein ⌇⌇ represents a single or double bond;

$R_1$ and $R_2$ are each independently is H or $—OR_5$;

$R_3$ is H, $—C(=O)(CH_2)_nCO_2H$ or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

$R_4$ is H or —OH;

$R_5$ is H, —C(=O)(CH$_2$)$_n$CO$_2$H or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

n is the integer 2, 3, 4, 5 or 6; and the stereoisomers, enantiomers and pharmaceutically acceptable salts thereof;

provided that $R_1$ and $R_2$ are H when $R_3$ is other than H.

2. A compound according to claim 1 wherein $R_1$ is —OR$_5$.

3. A compound according to claim 1 wherein $R_2$ is —OR$_5$.

4. A compound according to either claim 2 or claim 3 wherein $R_5$ is H.

5. A compound according to claim 1 wherein $R_4$ is —OH.

6. A compound according to claim 1 wherein $R_3$ is —C(=O)(CH$_2$)$_n$CO$_2$H.

7. A compound according to claim 6 wherein n is the integer 3.

8. A compound according to claim 1 wherein $R_1$ and $R_2$ are H.

9. A compound according to claim 1 wherein $R_1$ is H, $R_2$ is H, $R_3$ is H, $R_4$ is H and ∼∼∼ represents a double bond.

10. A compound of the formula:

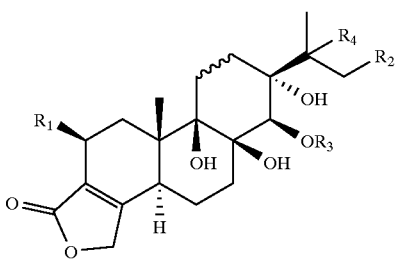

wherein ∼∼∼ represents a single or double bond;

$R_1$ and $R_2$ are each independently is H or —OR$_5$;

$R_3$ is H, —C(=O)(CH$_2$)$_n$CO$_2$H or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

$R_4$ is H or —OH;

$R_5$ is H, —C(=O)(CH$_2$)$_n$CO$_2$H or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

n is the integer 2, 3, 4, 5 or 6; and the stereoisomers, enantiomers and pharmaceutically acceptable salts thereof;

provided that $R_1$ and $R_2$ are H when $R_3$ is other than H.

11. A compound according to claim 10 wherein $R_1$ is —OR$_5$.

12. A compound according to claim 10 wherein $R_2$ is —OR$_5$.

13. A compound according to either claim 11 or claim 12 wherein $R_5$ is H.

14. A compound according to claim 10 wherein $R_4$ is —OH.

15. A compound according to claim 10 wherein $R_3$ is —C(=O)(CH$_2$)$_n$CO$_2$H.

16. A compound according to claim 15 wherein n is the integer 3.

17. A compound according to claim 10 wherein $R_1$ and $R_2$ are H.

18. A compound according to claim 10 wherein $R_1$ is H, $R_2$ is H, $R_3$ is H, $R_4$ is H and ∼∼∼ represents a double bond.

19. A compound of the formula:

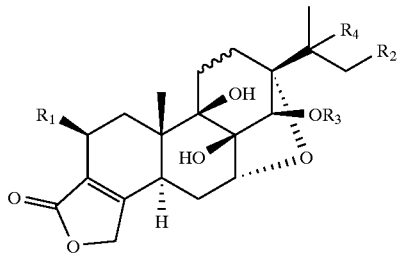

wherein ∼∼∼ represents a single or double bond;

$R_1$ and $R_2$ are each independently is H or —OR$_5$;

$R_3$ is H, —C(=O)(CH$_2$)$_n$CO$_2$H or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

$R_4$ is H or —OH;

$R_5$ is H, —C(=O)(CH$_2$)$_n$CO$_2$H or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

n is the integer 2, 3, 4, 5 or 6; and the stereoisomers, enantiomers and pharmaceutically acceptable salts thereof;

provided that $R_1$ and $R_2$ are H when $R_3$ is other than H.

20. A compound according to claim 19 wherein $R_1$ is —OR$_5$.

21. A compound according to claim 19 wherein $R_2$ is —OR$_5$.

22. A compound according to either claim 20 or claim 21 wherein $R_5$ is H.

23. A compound according to claim 19 wherein $R_4$ is —OH.

24. A compound according to claim 19 wherein $R_3$ is —C(=O)(CH$_2$)$_n$CO$_2$H.

25. A compound according to claim 24 wherein n is the integer 3.

26. A compound according to claim 19 wherein $R_1$ and $R_2$ are H.

27. A compound according to claim 19 wherein $R_1$ is H, $R_2$ is H, $R_3$ is H, $R_4$ is H and ∼∼∼ represents a double bond.

28. A method of treating a patient suffering from an autoimmune disease comprising administering to a patient an effective amount of a compound of the formula:

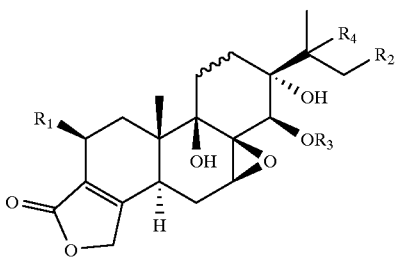

wherein ∼ represents a single or double bond;

$R_1$ and $R_2$ are each independently is H or $-OR_5$;

$R_3$ is H, $-C(=O)(CH_2)_nCO_2H$ or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

$R_4$ is H or $-OH$;

$R_5$ is H, $-C(=O)(CH_2)_nCO_2H$ or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

n is the integer 2, 3, 4, 5 or 6; and the stereoisomers, enantiomers and pharmaceutically acceptable salts thereof;

provided that $R_1$ and $R_2$ are H when $R_3$ is other than H.

29. A method according to claim 28 wherein the autoimmune disease is rheumatoid arthritis.

30. A method according to claim 29 wherein $R_1$ is H, $R_2$ is H, $R_3$ is H, $R_4$ is H and ∼ represents a double bond.

31. A method of treating a patient suffering from an autoimmune disease comprising administering to a patient an effective amount of a compound of the formula:

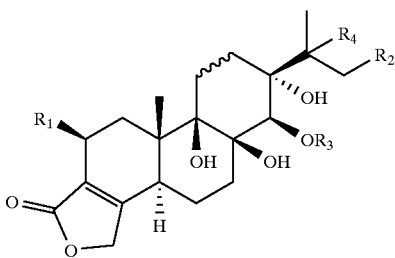

wherein ∼ represents a single or double bond;

$R_1$ and $R_2$ are each independently is H or $-OR_5$;

$R_3$ is H, $-C(=O)(CH_2)_nCO_2H$ or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

$R_4$ is H or $-OH$;

$R_5$ is H, $-C(=O)(CH_2)_nCO_2H$ or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

n is the integer 2, 3, 4, 5 or 6; and the stereoisomers, enantiomers and pharmaceutically acceptable salts thereof;

provided that $R_1$ and $R_2$ are H when $R_3$ is other than H.

32. A method according to claim 31 wherein the autoimmune disease is rheumatoid arthritis.

33. A method according to claim 32 wherein $R_1$ is H, $R_2$ is H, $R_3$ is H, $R_4$ is H and ∼ represents a double bond.

34. A method of treating a patient suffering from an autoimmune disease comprising administering to a patient an effective amount of a compound of the formula:

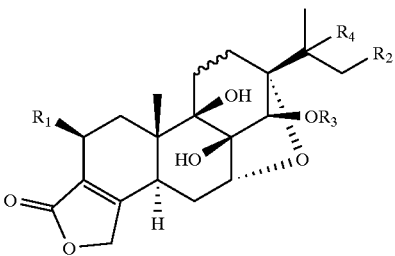

wherein ∼ represents a single or double bond;

$R_1$ and $R_2$ are each independently is H or $-OR_5$;

$R_3$ is H, $-C(=O)(CH_2)_nCO_2H$ or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

$R_4$ is H or $-OH$;

$R_5$ is H, $-C(=O)(CH_2)_nCO_2H$ or a suitable amino acid selected from the group consisting of alanine, arginine, asparagine, aspartic acid, cysteine glutamine, glutamic acid, glycine, histidine, isoleucine, leucine, lysine, methionine, phenylalanine, proline, serine, threonine, tryptophan, tyrosine and valine;

n is the integer 2, 3, 4, 5 or 6; and the stereoisomers, enantiomers and pharmaceutically acceptable salts thereof.

35. A method according to claim 34 wherein the autoimmune disease is rheumatoid arthritis.

36. A method according to claim 35 wherein $R_1$ is H, $R_2$ is H, $R_3$ is H, $R_4$ is H and ∼ represents a double bond.

* * * * *